(12) United States Patent
Fujishita et al.

(10) Patent No.: US 6,809,101 B2
(45) Date of Patent: Oct. 26, 2004

(54) COMPOUNDS HAVING ANTI-HEPATITIS C VIRUS EFFECT

(75) Inventors: Toshio Fujishita, Osaka (JP); Kenji Abe, Settsu (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 10/362,368

(22) PCT Filed: Aug. 29, 2001

(86) PCT No.: PCT/JP01/07411

§ 371 (c)(1),
(2), (4) Date: Feb. 27, 2003

(87) PCT Pub. No.: WO02/20497

PCT Pub. Date: Mar. 14, 2002

(65) Prior Publication Data

US 2003/0203948 A1 Oct. 30, 2003

(30) Foreign Application Priority Data

Sep. 1, 2000 (JP) .......................... 2000-264920

(51) Int. Cl.[7] .................. C07D 277/34; C07D 277/36; C07D 417/06; A31K 31/426; A31K 31/4439
(52) U.S. Cl. .................. 514/255.05; 514/256; 514/342; 514/369; 514/389; 544/333; 544/405; 546/269.7; 548/183; 548/316.1
(58) Field of Search .................. 544/333, 405; 546/269.7; 548/183, 316.1; 514/255.05, 256, 342, 369, 389

(56) References Cited

FOREIGN PATENT DOCUMENTS

JP          61-56175 A      3/1986

OTHER PUBLICATIONS

Kvitko I. Ya, et al., "C–Acylation of Rhodanine Derivatives," *Khimiya Geterotsiklicheskikh Soedinenij*, 1972, vol. 11, pp. 1491–3495.
Ramirez Fausto, et al., "New Syntheses of 5–Acyihydaritoins and of 5–Acyl–4–Hydroxyoxazojes Precursors of β–oxo–α–amino Acids and of β–oxo–α–hydroxy Acid Amides," *Tetrahedron*, 1969, vol.25, No.4, pp.771–782.

*Primary Examiner*—Fiona T. Powers
(74) *Attorney, Agent, or Firm*—Foley & Lardner LLP

(57) ABSTRACT

It is found out that compounds represented by the formula (I):

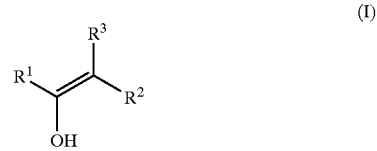

wherein $R^1$ is an optionally substituted carbocyclic group or an optionally substituted heterocyclic group; and $R^2$ and $R^3$ taken together with the adjacent carbon atom form an optionally substituted heterocyclic group having one or more of oxo and/or thioxo; have an HCV RNA-dependent RNA synthase inhibitory effect.

18 Claims, No Drawings

US 6,809,101 B2

COMPOUNDS HAVING ANTI-HEPATITIS C VIRUS EFFECT

TECHNICAL FIELD

The present invention relates to a treating agent against hepatitis C, in detail an anti-hepatitis C virus agent, a nucleic acid polymerase inhibitor, and a RNA-dependent RNA polymerase inhibitor.

BACKGROUND ART

It is supposed that there are one to two hundred million people infected with hepatitis C virus (hereafter called as HCV) worldwide, and over 1.5 million people infected with HCV in Japan. Approximately 50% of them become chronic hepatitis, and approximately 20% thereof become liver cirrhosis or hepatocellular carcinoma after 30 years or more of the infection. In Japan, twenty and several thousand people die every year due to hepatocellular carcinoma caused by HCV infection. At present, interferon α is used widely as a treating agent against hepatitis C, however, percentage of successful treatment is only 20% to 30% and its side effect is strong. It is expected to develop a more useful and more safety treating agent.

The anti-HCV agents are targeted on protease, RNA helicase, RNA-dependent RNA polymerase, and the like, and as the RNA-dependent RNA polymerase inhibitor known are cerulenin, gliotoxin, and dioxobutyric acid ((1) Antiviral Res., 41, 65 (1999), (2) Antiviral Ther., 3 (Suppl 3), 99 (1998), (3) WO00/06529).

On the other hand, as an acylthiazolidinedione derivative similar to a compound of the present invention, a compound wherein the acyl group is a substituted benzoyl group is described in (1) Strukt. Mekh. Deistviya Fiziol. Aktiv. Veschestv (1972) 92-92, (2) Khim. Geterotsikl. Soedin. (1972), (11), 1492–1495. However, in these references a concrete medical use is not described. Furthermore, a compound wherein the acyl group is a substituted heteroarylcarbonyl group is not; described therein at all.

DISCLOSURE OF INVENTION

The development of a treating agent against hepatitis C, especially an HCV RNA-dependent RNA polymerase inhibitor, is expected.

It is found that an acylthiazolidinedione derivative and the like have an HCV RNA-dependent RNA polymerase inhibitory effect.

That is, the present invention relates to:

(1) A treating agent against hepatitis C virus which contains as an active ingredient a compound of the formula (I), a tautomer, a prodrug, a pharmaceutically acceptable salt, or a solvate thereof:

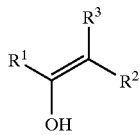

wherein $R^1$ is an optionally substituted carbocyclic group or an optionally substituted heterocyclic group; $R^2$ and $R^3$ taken together with the adjacent carbon atom form an optionally substituted heterocyclic group having one or more of oxo and/or thioxo, (2) A treating agent against hepatitis C virus as described in (1) wherein $R^1$ is optionally substituted heteroaryl or optionally substituted aryl; $R^2$ and $R^3$ taken together with the adjacent carbon atom form a group of the formula (A):

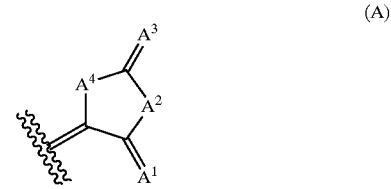

wherein $A^1$ and $A^3$ are each independently oxygen atom or sulfur atom; $A^2$ and $A^4$ are each independently —O—, —S—, or —NR$^4$— wherein $R^4$ is hydrogen, optionally substituted alkyl, optionally substituted acyl, optionally substituted aryl, or optionally substituted aralkyl, (3) A treating agent against hepatitis C virus as described in (2) wherein $A^1$ is oxygen atom; $A^2$ is —NH—; $A^1$ and $A^4$ are sulfur atom, (4) A compound of the formula (II):

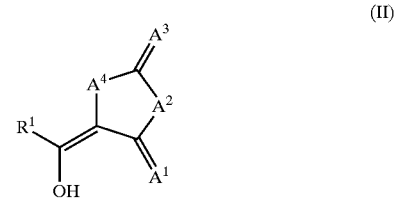

wherein $R^1$ is optionally substituted carbocyclic group or optionally substituted heterocyclic group; $A^1$ and $A^3$ are each independently oxygen atom or sulfur atom; $A^2$ is —NR$^4$— wherein $R^4$ is hydrogen, optionally substituted alkyl, optionally substituted acyl, optionally substituted aryl, or optionally substituted aralkyl, provided that when $R^1$ is optionally substituted aryl, $R^4$ is hydrogen or optionally substituted alkyl; $A^4$ is —S—; and provided that the following compounds are excluded wherein $A^1$ is oxygen atom, $A^2$ is —NEt-, $A^3$ is sulfur atom, and $R^1$ is 4-bromophenyl, 4-n-butoxycarbonylphenyl, 4-methoxyphenyl, 3-nitrophenyl, 4-nitrophenyl, 3-methylphenyl, 4-methylphenyl, 4-chlorophenyl or phenyl; $A^1$ is oxygen atom, $A^2$ is —NH—, $A^3$ is sulfur atom, and $R^1$ is 2-thiocarboxyphenyl or 2-carboxyphenyl; and $A^1$ is oxygen atom, $A^2$ is —NH—, $A^1$ is oxygen atom, and $R^1$ is 2-carboxyphenyl;
a tautomer, a prodrug, a pharmaceutically acceptable salt, or a solvate thereof, (5) A compound of (4) wherein $R^1$ is optionally substituted heteroaryl;
a tautomer, a prodrug, a pharmaceutically acceptable salt, or a solvate thereof, (6) A compound of (4) wherein $R^1$ is non-substituted heteroaryl or heteroaryl substituted with alkyl, alkoxy, hydroxy, halogen, trityl, alkoxyalkoxy, cyanoallylalkoxy, cyanoalkoxy, hydroxyalkyl, cyanoalkyl, carboxy or alkoxycarbonyl;
a tautomer, a prodrug, a pharmaceutically acceptable salt, or a solvate thereof, (7) A compound of (5) or (6) wherein $R^1$ is optionally substituted 5-membered heteroaryl;
a tautomer, a prodrug, a pharmaceutically acceptable salt, or a solvate thereof, (8) A compound of (5) or (6) wherein $R^1$ is optionally substituted furyl, optionally substituted t-hienyl, optionally substituted pyrrolyl, optionally substituted imidazolyl, optionally substituted oxazolyl, optionally substituted isoxazolyl, optionally substituted triazolyl, optionally substituted oxadiazolyl, optionally substituted tetrazolyl, optionally substituted pyridyl, optionally substituted benzofuryl, optionally substituted pyrimidinyl, optionally substituted pyrazinyl, or optionally substitutec(thiazolyl;

a tautomer, a prodrug, a pharmaceutically acceptable salt, or a solvate thereof, (9) A compound of (4) wherein $R^1$ is optionally substituted aryl;

a tautomer, a prodrug, a pharmaceutically acceptable salt, or a solvate thereof,

(10) A compound of any one of (4) to (9) wherein $A^2$ is —NH—;

a tautomer, a prodrug, a pharmaceutically acceptable salt, or a solvate thereof,

(11) A compound of any one of (4) to (10) wherein $A^1$ is oxygen atom; $A^3$ is sulfur atom;

a tautomer, a prodrug, a pharmaceutically acceptable salt, or a solvate thereof,

(12) A compound of any one of (4) to (9) wherein $A^1$ is oxygen atom; $A^2$ is —NH—; $A^3$ is sulfur atom; $A^4$ is —S—;

a tautomer, a prodrug, a pharmaceutically acceptable salt, or a solvate thereof,

(13) A pharmaceutical composition which contains as an active ingredient a compound of any one of (4) to (12), a tautomer, a prodrug, a pharmaceutically acceptable salt, or a solvate thereof,

(14) A pharmaceutical composition of (13) as a treating agent against hepatitis C,

(15) A pharmaceutical composition of (13) as an anti-hepatitis C virus agent,

(16) A pharmaceutical composition of (13) as a nucleic acid polymerase inhibitor,

(17) A pharmaceutical composition of (13) as a RNA-dependent RNA polymerase inhibitor,

(18) A method of treating hepatitis C comprising administration of a treating agent against hepatitis C of (1),

(19) Use of a compound of (1) for the preparation of a treating agent against hepatitis C, The present invention has found that a compound of the formula (I), a tautomer, a prodrug, a pharmaceutically acceptable salt, or a solvate thereof:

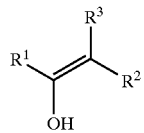

(I)

wherein $R^1$ is an optionally substituted carbocyclic group or an optionally substituted heterocyclic group; $R^2$ and $R^3$ taken together with the adjacent carbon atom form an optionally substituted heterocyclic group having one or more of oxo and/or thioxo; exhibits an inhibitory effect against nucleic acid polymerase, in detail an inhibitory effect against RNA-dependent RNA polymerase, and inhibits the increase of HCV, whereby to provide a treating agent against HCV containing these compounds or the like.

A characteristic of the compounds used in the present invention is that the group represented by $R^1$, and an optionally substituted heterocyclic group having one or more of oxo and/or thioxo which is formed by $R^2$ and $R^3$ taken together with the adjacent carbon atom are substituted on a group of the formula:

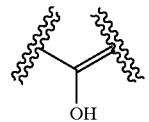

Especially, as a compound of the formula (1) the following cases are preferred.

wherein $R^1$ is optionally substituted heteroaryl or optionally substituted aryl, wherein $R^1$ is optionally substituted heteroaryl, wherein $R^1$ is non-substituted heteroaryl or heteroaryl optionally substituted with alkyl, alkoxy, hydroxy, halogen, trityl, alkoxyalkyl, cyanoarylalkoxy, cyanoalkoxy, hydroxyalkyl, cyanoalkyl, carboxy, or alkoxycarbonyl, wherein $R^1$ is optionally substituted 5-membered heteroaryl, wherein $R^1$ is optionally substituted furyl, optionally substituted thienyl, optionally substituted pyrrolyl, optionally substituted imidazolyl, optionally substituted oxazolyl, optionally substituted isoxazolyl, optionally substituted triazolyl, optionally substituted oxadiazolyl, optionally substituted tetrazolyl, optionally substituted pyridyl, optionally substituted benzofuryl, optionally substituted pyrimidinyl, optionally substituted pyrazinyl, or optionally substituted thiazolyl, wherein $R^1$ is optionally substituted 5-membered aryl, wherein $R^2$ and $R^3$ taken together with the adjacent carbon atom form a group of the formula (A):

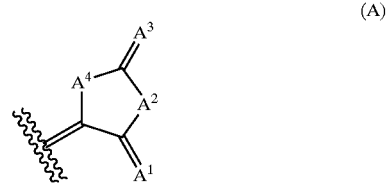

(A)

wherein $A^1$ and $A^3$ are each independently oxygen atom or sulfur atom; $A^2$ and $A^4$ are each independently —O—, —S—, or —NR$^4$— wherein $R^4$ is hydrogen, optionally substituted alkyl, optionally substituted acyl, optionally substituted aryl, or optionally substituted aralkyl.

In a group shown by the above (A), preferred are those.

wherein $A^1$ and $A^3$ are each independently oxygen atom or sulfur atom; $A^2$ is —NR$^4$— wherein $R^4$ is hydrogen, optionally substituted alkyl, optionally substituted acyl, optionally substituted aryl, or optionally substituted aralkyl; $A^4$ is —S—, wherein $A^1$ is oxygen atom; $A^2$ is —NH—; $A^1$ is sulfur atom; $A^4$ is —S—, wherein $A^2$ is —NH—, wherein $A^1$ is oxygen atom; $A^3$ is sulfur atom, or wherein $A^1$ is oxygen atom; $A^2$ is —NH—; $A^3$ is sulfur atom; $A^4$ is —S—.

Especially, preferable is a compound of the formula (II):

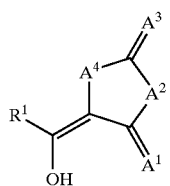

(II)

wherein R¹ is an optionally substituted carbocyclic group or an optionally substituted heterocyclic group; A¹ and A³ are each independently oxygen atom or sulfur atom; A² is —NR⁴— wherein R⁴ is hydrogen, optionally substituted alkyl, optionally substituted acyl, optionally substituted aryl, or optionally substituted aralkyl, provided that when R¹ is an optionally substituted aryl, R⁴ is hydrogen or optionally substituted alkyl; A⁴ is sulfur atom.

Each term employed alone or in combination with other terms has the following means.

The term "carbocyclic group" means cycloalkyl, cycloalkenyl, or aryl. Especially, aryl is preferred.

The term "cycloalkyl" means a cycloalkyl having 3 to 10 carbon atoms. Examples of cycloalkyl include cyclopropyl, cyclobutyl, cyclopentyl, cyclohexyl, cycloheptyl, cyclooctyl, and the like. Cyclopentyl and cyclohexyl are preferred.

The term "cycloalkenyl" means a cycloalkenyl having 3 to 10 carbon atoms. Examples of cycloalkenyl include 1-cyclopropenyl, 1-cyclobutenyl, 1-cyclopentenyl, 1-cyclohexenyl, 1-cycloheptenyl, 1-cyclooctenyl, and the like. 1-Cyclopentenyl and 1-cyclohexenyl are preferred.

The term "aryl" means monocyclic or condensed ring aromatic carbocyclic group having 6 to 14 carbon atoms. Examples of aryl include phenyl, 1-naphtyl, 2-naphtyl, 1-anthryl, 2-anthryl, 9-anthryl, 1-phenanthryl, 2-phenanthryl, 3-phenanthryl, 4-phenanthryl, 9-phenanthryl, and the like. Phenyl, 1-naphtyl, and 2-naphtyl are preferred.

The term "herterocyclic group" for R¹ means heteroaryl and non-aromatic herterocyclic group. Especially, heteroaryl is preferred.

The term "heteroaryl" herein used means a 5 to 7 membered aromatic heterocyclic group which contains one or more of nitrogen, oxygen, and sulfur atoms in the ring, or an aromatic cyclic group fused with one or more aromatic carbocyclic group or other aromatic heterocyclic group. The "heteroaryl" may have a bond ragical at any substitutable position, for example at a carbon or nitrogen atom in the aromatic heterocyclic group or aromatic carbocyclic group. Examples of the heteroaryl include furyl (e.g., 2-furyl, 3-furyl), thienyl (e.g., 2-thienyl 3-thienyl), pyrrolyl (e.g., 1-pyrrolyl, 2-pyrrolyl, 3-pyrrolyl), pyridyl (e.g., 2-pyridyl, 3-pyridyl, 4-pyridyl), oxazolyl (e.g., 2-oxazolyl, 4-oxazolyl, 5-oxazolyl), isoxazolyl (e.g., 3-isoxazolyl, 4-isoxazolyl, 5-isoxazolyl), thiazolyl (e.g., 2-thiazolyl, 4-thiazolyl, 5-thiazolyl), isothiazolyl (e.g., 3-isothiazolyl, 4-isotbiazolyl, 5-isothiazolyl), imidazolyl (e.g., 1-imidazolyl, 2-imidazolyl, 4-imidazolyl), triazolyl (e.g., 1,2,4-triazol-1-yl, 1,2,4-triazol-3-yl, 1,2,4-triazol-4-yl), oxadiazolyl (e.g., 1,3,4-oxadiazol-2-yl), tetrazolyl (e.g., 1-tetrazolyl, 2-tetrazolyl, 5-tetrazolyl), pyrazolyl (e.g., 1-pyrazolyl, 3-pyrazolyl, 4-pyrazolyl), furazanyl (e.g., 3-furazanyl), pyridazinyl (e.g., 3-pyridazinyl, 4-pyridazinyl), pyrimidinyl (e.g., 2-pyrimidinyl, 4-pyrimidinyl, 5-pyrimidinyl), pyrazinyl (e.g., 2-pyrazinyl), indolyl (e.g., 1-indolyl, 2-indolyl, 3-indolyl, 4-indolyl, 5-indolyl, 6-indolyl, 7-indolyl), benzothienyl (e.g., 2-benzo[b]thienyl, 3-benzo[b]thienyl, 4-benzo[b]thienyl, 5-benzo[b]thienyl, 6-benzo[b]thienyl, 7-benzo[b]thienyl), benzofuryl (e.g., 2-benzo[b]furyl, 3-benzo[b]furyl, 4-benzo[b]furyl, 5-benzo[b]furyl, 6-benzo[b]furyl, 7-benzo[b]furyl), benzimidazolyl (e.g., 1-benzimidazolyl, 2-benzimidazolyl, 4-benzimidazolyl, 5-benzimidazolyl), quinolyl (e.g., 2-quinolyl, 3-quinolyl, 4-quinolyl, 5-quinolyl, 6-quinolyl, 7-quinolyl, 8-quinolyl), isoquinolyl (e.g., 1-isoquinolyl, 3-isoquinolyl, 4-isoquinolyl, 5-isoquinolyl, 6-isoquinolyl, 7-isoquinolyl, 8-isoquinolyl), cinnolinyl (e.g., 3-cinnolinyl, 4-cinnolinyl, 5-cinnolinyl, 6-cinnolinyl, 7-cinnolinyl, 8-cinnolinyl), quinazolinyl (e.g., 2-quinazolinyl, 4-quinazolinyl, 5-quinazolinyl, 6-quinazolinyl, 7-quinazolinyl, 8-quinazolinyl), quinoxalinyl (e.g., 2-quinoxalinyl, 5-quinoxalinyl, 6-quinoxalinyl), phthalazinyl (e.g., 1-phthalazinyl, 5-phthalazinyl, 6-phthalazinyl), pteridinyl (e.g., 2-pteridinyl, 4-pteridinyl, 6-pteridinyl, 7-pteridinyl), acridinyl (e.g., 1-acridinyl, 2-acridinyl, 3-acridinyl, 4-acridinyl, 9-acridinyl), phenazinyl (e.g., 1-phenazinyl, 2-phenazinyl), phenothiazinyl (e.g., 1-phenothiazinyl, 2-phenothiazinyl, 3-phenothiazinyl, 4-phenothiazinyl), and the like.

"5-Membered heteroaryl" is preferred. Examples of the 5-membered heteroaryl include furyl (e.g., 2-furyl, 3-furyl), thienyl (e.g., 2-thienyl 3-thienyl), pyrrolyl (e.g., 1-pyrrolyl, 2-pyrrolyl, 3-pyrrolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), thiazolyl (e.g., 2-thiazolyl, 4-thiazolyl, 5-thiazolyl), isothiazolyl (e.g., 3-isothiazolyl, 4-isothiazolyl, 5-isothiazolyl), imidazolyl (e.g., 1-imidazolyl, 2-imidazolyl, 4-imidazolyl), triazolyl (e.g., 1,2,4-triazol-1-yl, 1,2,4-triazol-3-yl, 1,2,4-triazol-4-yl), oxadiazolyl (e.g., 1,3,4-oxadiazol-2-yl), tetrazolyl (e.g., 1-tetrazolyl, 2-tetrazolyl, 5-tetrazolyl), pyrazolyl (e.g., 1-pyrazolyl, 3-pyrazolyl, 4-pyrazolyl), furazanyl (e.g., 3-furazanyl), and the like. Especially, are preferred furyl (e.g., 2-furyl, 3-furyl), thienyl (e.g., 2-thienyl 3-thienyl), pyrrolyl (e.g., 1-pyrrolyl, 2-pyrrolyl, 3-pyrrolyl), imidazolyl (e.g., 1-imidazolyl, 2-imidazolyl, 4-imidazolyl), oxazolyl (e.g., 2-oxazolyl, 4-oxazolyl, 5-oxazolyl), isoxazolyl (e.g., 3-isoxazolyl, 4-isoxazolyl, 5-isoxazolyl), triazolyl (e.g., 1,2,4-triazol-1-yl, 1,2,4-triazol-3-yl, 1,2,4-triazol-4-yl), oxadiazolyl (e.g., 1,3,4-oxadiazol-2-yl), tetrazolyl (e.g., 1-tetrazolyl, 2-tetrazolyl, 5-tetrazolyl), pyridyl (e.g., 2-pyridyl, 3-pyridyl, 4-pyridyl), benzofuryl (e.g., 2-benzo[b]furyl, 3-benzo[b]furyl, 4-benzo[b]furyl, 5-benzo[b]furyl, 6-benzo[b]furyl, 7-benzo[b]furyl), pyrimidinyl (e.g., 2-pyrimidinyl, 4-pyrimidinyl, 5-pyrimidinyl), pyrazinyl (e.g., 2-pyrazinyl), thiazolyl (e.g., 2-thiazolyl, 4-thiazolyl, 5-thiazolyl), and the like.

The term "non-aromatic heterocyclic group" herein used means a non-aromatic heterocyclic group which contains one or more hetero atoms selected from the group consisting of nitrogen, oxygen, and sulfur atoms in the ring, and the group has a bond radical at any substitutable position. Examples of the non-aromatic heterocyclic group include 1-pyrrolinyl, 2-pyrrolinyl, 3-pyrrolinyl, 1-pyrrolidinyl, 2-pyrrolidinyl, 3-pyrrolidinyl, 1-imidazolinyl, 2-imidazolinyl, 4-imidazolinyl, 1-imidazolidinyl, 2-imidazolidinyl, 4-imidazolidinyl, 1-pyrazolinyl, 3-pyrazolinyl, 4-pyrazolinyl, 1-pyrazolidinyl, 3-pyrazolidinyl, 4-pyrazolidinyl, piperidino, 2-piperidinyl, 3-piperidinyl, 4-piperidinyl, 1-piperazinyl, 2-piperazinyl, 2-morpholinyl, 3-morpholinyl, morpholino, tetrahydropyranyl, oxazolinyl, and the like. Further, "non-aromatic heterocyclic group" may be saturated or unsaturated.

Further, "carbocyclic group" and "heterocyclic group" for R¹ may be fused additionally with a carbocycle or heterocycle. The term "carbocycle" means carbocycle corresponding to the above mentioned "carbocyclic group". Examples of carbocycle include cyclobutane, cyclopentane, cyclohexane, cycloheptane, benzene, naphthalene, and the like. The term "heterocycle" means heterocycle corresponding to the above mentioned "heterocyclic group". Examples of heterocycle are pyrrolidine, piperadine, oxolane, 1,3-dioxolane, 1,4-dioxolane, thiolane, thiophen, furan, pyrrole, pyridine, and the like.

These carbocycle and heterocycle may be fused additionally with carbocycle or heterocycle.

Examples of the above "carbocyclic group" or "heterocyclic group" which are fused with carbocycle or heterocycle are as follows.

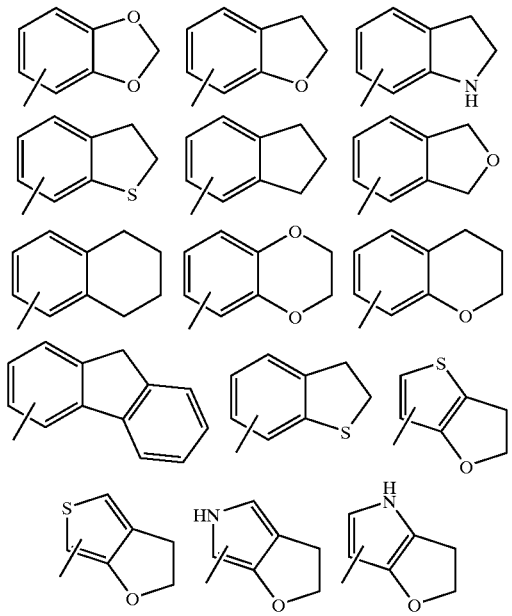

The term "heterocyclic group having one or more oxo or thioxo" means heterocyclic group having 1 to 3 oxo or thioxo at any possible position in the ring. Especially, 5- or 6-membered heterocyclic group having oxo or thioxo at a neighboring position of the bond radical is preferred and exemplified below.

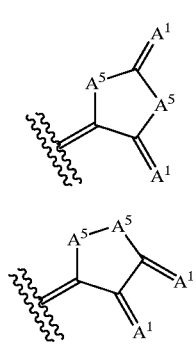

(A)

(B)

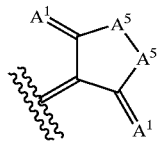

(C)

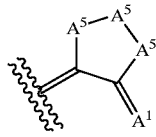

(D)

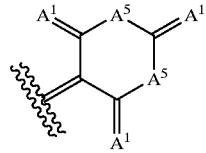

(E)

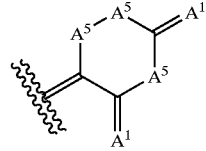

(F)

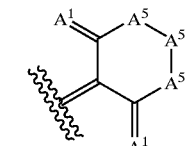

(G)

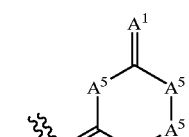

(H)

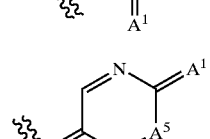

(J)

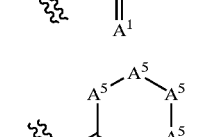

(K)

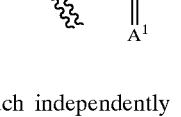

wherein A¹ is each independently oxygen atom or sulfur atom; A⁵ is each independently —O—, —S—, —NR⁴— wherein R⁴ is hydrogen, optionally substituted alkyl, optionally substituted acyl, optionally substituted aryl, or optionally substituted aralkyl, or —CH₂—, provided that one or more of A⁵ is —O—, —S—, —NR⁴— wherein R⁴ is hydrogen, optionally substituted alkyl, optionally substituted acyl, optionally substituted aryl, or optionally substituted aralkyl.

Among the above, preferable is a group represented by the formula (A):

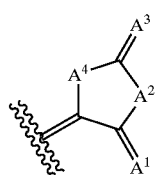

(A)

and more preferable is that wherein $A^1$ and $A^3$ are each independently oxygen atom or sulfur atom; $A^2$ and $A^4$ are each independently —O—, —S—, or —$NR^4$— wherein $R^4$ is hydrogen, optionally substituted alkyl, optionally substituted acyl, optionally substituted aryl, or optionally substituted aralkyl.

Especially, preferable is a compound of the formula (II):

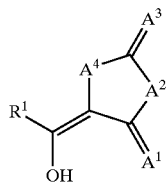

(II)

wherein $R^1$ is optionally substituted carbocyclic group or optionally substituted heterocyclic group; $A^1$ and $A^3$ are each independently oxygen atom or sulfur atom; $A^2$ is —$NR^4$— wherein $R^4$ is hydrogen, optionally substituted alkyl, optionally substituted acyl, optionally substituted aryl, or optionally substituted aralkyl, provided that when $R^1$ is optionally substituted aryl, $R^4$ is hydrogen or optionally substituted alkyl; $A^4$ is —S—; and provided that the following compounds are excluded wherein $A^1$ is oxygen atom, $A^2$ is —NEt-, $A^3$ is sulfur atom, and $R^1$ is 4-bromophenyl, 4-n-butoxycarbonylphenyl, 4-methoxyphenyl, 3-nitrophenyl, 4-nitrophenyl, 3-methylphenyl, 4-methylphenyl, 4-chlorophenyl or phenyl; $A^1$ is oxygen atom, $A^2$ is —NH—, $A^3$ is sulfur atom, and $R^1$ is 2-thiocarboxyphenyl or 2-carboxyphenyl; and $A^1$ is oxygen atom, $A^2$ is —NH—, $A^3$ is oxygen atom, and $R^1$ is 2-carboxyphenyl.

Substituents of "optionally substituted alkyl" and "optionally substituted acyl" include, for example, alkyl, alkenyl, alkynyl, cycloalkyl, halogen, hydroxy, carboxy, formyloxy, formyl, haloformyl, oxalo, mercapto, thioformyl, thiocarboxy, dithiocarboxy, thiocarbamoyl, sulfino, sulfo, sulfamoyl, sulfoamino, optionally substituted amino, cyano, isocyano, cyanato, isocyanato, thiocyanato, isothiocyanato, hydroxyamino, carbamoyl, nitroso, nitro, hydrazino, azide, ureido, amidino, guanidino, and the like. Especially, cycloalkyl, halogen, hydroxy, carboxy, optionally substituted amino, cyano, and the like are preferred. And unsubstituted one is preferred.

These substituents may be at 1 to 3 any substitutable position(s) in the above mentioned alkyl and the above mentioned acyl.

Substituents of "optionally substituted carbocyclic group", "optionally substituted heterocyclic group", "optionally substituted aryl", "optionally substituted aralkyl" and "optionally substituted heteroaryl" include, for example, alkyl, alkenyl, alkynyl, cycloalkyl, halogen, hydroxy, carboxy, formyloxy, formyl, haloformyl, oxalo, mercapto, thioformyl, thiocarboxy, dithiocarboxy, thiocarbamoyl, sulfino, sulfo, sulfamoyl, sulfoamino, optionally substituted amino, cyano, isocyano, cyanato, isocyanato, thiocyanato, isothiocyanato, hydroxyamino, carbamoyl, nitroso, nitro, hydrazino, azide, ureido, amidino, guanidino, trityl, alkoxyalkyl, cyanoarylalkoxy, cyanoalkoxy, hydroxyalkyl, cyanoalkyl, carboxy, and alkoxycarbonyl, and the formula: —$Z^1$–$Z^2$ wherein $Z^1$ is a single bond, —O—, —C(=O)—O—, —O—C(=O)—, —C(=O)—, —C(=O)—C(=O)—, —C(=O).C(=O)—O—, —$CH_2$—C(=O)—, —S—, —$SO_2$—, —SO—, —C(=S)—, —NH—, —$NZ^3$—, —NH—C(=O)—, —C(=O)—NH—, —$NZ^3$—C(=O)—, —C(=O)—$NZ^3$—, —N=N—, —NH—C(=O)—O—, —NH—$SO_2$—, —$SO_2$—NH—, —$NZ^3$—$SO_2$— or —$SO_2$—$NZ^3$—; $Z^2$ and $Z^3$ are each independently alkyl, alkenyl, alkynyl, haloalkyl, hydroxyalkyl, optionally substituted aminoalkyl, carbocyclic group optionally substituted with alkyl, hydroxy or halogen, heterocyclic group optionally substituted with alkyl, hydroxy or halogen, arylalkyl optionally substituted with alkyl, hydroxy or halogen, or heteroarylalkyl optionally substituted with alkyl, hydroxy or halogen, and the like. Especially, preferred are alkyl, alkoxy, hydroxy, halogen, trityl, alkoxyalkoxy, cyanoarylalkoxy, cyanoalkoxy, hydroxyalkyl, cyanoalikyl, carboxy and alkoxycarbonyl. And unsubstituted one is preferred.

These substituents may be at 1 to 5 any substitutable position(s) in the above mentioned carbocyclic group, the above mentioned heterocyclic group, the above mentioned aryl, the above mentioned aralkyl and the above mentioned heteroaryl.

The term "alkyl" herein used means a straight or branched chain alkyl having 1 to 8 carbon atom(s). Examples of alkyl include methyl, ethyl, n-propyl, isopropyl, n-butyl, isobutyl, sec-butyl, tert-butyl, n-pentyl, isopentyl, neo-pentyl, t-pentyl, n-hexyl, isohexyl, n-heptyl, n-octyl, n-nonanyl, and the like.

The term "alkenyl" herein used means a straight or branched chain alkenyl having 2 to 8 carbon atoms and one or more double bonds. Examples of the alkenyl include vinyl, 1-propenyl, 2-propenyl, isopropenyl, and the like.

The term "lower alkynyl" herein used means a straight or branched chain alkynyl having 2 to 8 carbon atoms and one or more triple bond. Examples of the alkynyl include ethynyl, 1-propynyl, 2-propynyl, 1-butynyl, 2-butynyl, 3-butynyl, and the like.

Alkyl consisted in "alkoxy" is defined as the above "alkyl", examples of alkoxy include methoxy, ethoxy, n-propoxy, isopropoxy, n-butoxy, isobutoxy, tert-butoxy, and the like. Especially, methoxy and ethoxy are preferred.

The term "acyl" herein used means carbonyl substituted with the above-mentioned "alkyl" and the above-mentioned "aryl". Examples of acyl include acetyl, propyonyl, butyryl, isobutyryl, valeryl, isovaleryl, pivaloyl, hexanoyl, octanoyl, benzoyl, 1-naphthoyl, 2-naphthoyl, and the like. Especially, acetyl and benzoyl are preferred.

The term "halogen" herein used means fluoro, chloro, bromo, and iodo.

The term "haloalkyl" herein used means the above-mentioned "alkyl" which is one or more substituted with halogen. Examples of the haloalkyl include chloromethyl, fluoromethyl, trifluoromethyl, 2,2,2-trifluoroethyl, 1,1-difluoroethyl, trichloromethyl, 2,2,2-trichloroethyl, 1,1-dichloroethyl, and the like.

The term "hydroxyalkyl" herein used means the above-mentioned "alkyl" which is one or two substituted with hydroxy. Examples of the hydroxyalkyl include hydroxymethyl, 1-hydroxyethyl, 2-hydroxyethyl, 1,1-dihydroxyethyl, 1,2-dihydroxyethyl, 1,2-dihydroxy-n-propyl, and the like.

The term "aminoalkyl" herein used means the above-mentioned "alkyl" which is one or two substituted with amino. Examples of the aminoalkyl include aminomethyl, 1-aminoethyl, 2-aminoethyl, 1,1-diaminoethyl, 1,2-diaminoethyl, 1,2-diamino-n-propyl, and the like.

Substituents of "optionally substituted amino" and "optionally substituted aminoalkyl" include, for example, the above-mentioned "alkyl", the above-mentioned "arylalkyl", the above-mentioned "carbocyclic group", the above-mentioned "heterocyclic group", the above-mentioned "heteroarylalkyl", and the like. They may be mono- or di-substituted with these substituents. Further, when they are di-substituted with "alkyl", may form a ring taken together nitrogen atom of amino group.

Examples of "optionally substituted amino" include amino, methylamino, dimethylamino, methylethylamino, diethylamino, pyrrolidino, piperidino, phenylmethylamino, isopropylamino, diisopropylamino, and the like.

Examples of "optionally substituted aminoalkyl" include aminomethyl, dimethylaminomethyl, methylaminomethyl, methylethylaminomethyl, diethylaminomethyl, pyrrolidinomethyl, piperidinomethyl, phenylmethylaminomethyl, isopropylaminomethyl, diisopropylaminomethyl, and the like.

The term "alkoxyalkoxy" herein used means the above-mentioned alkoxy substituted with the above-mentioned alkoxy, examples of alkoxyalkoxy include methoxymethoxy, ethoxymethoxy, n-propoxymethoxy, isopropoxymethoxy, n-butoxymethoxy, isobutoxymethoxy, tert-butoxymethoxy, and the like. Especially, methoxymethoxy and ethoxymethoxy are preferred.

The term "cyanoarylalkoxy" herein used means the above-mentioned alkoxy substituted the above-mentioned aryl substituted with cyano, examples of cyanoarylalkoxy include 2-cyanobenzyloxy and the like.

The term "cyanoalkoxy" herein used means the above-mentioned alkoxy substituted with cyano, examples of cyanoalkoxy include 3-cyano-n-propoxy and the like.

The term "cyanoalkyl" herein used means the above-mentioned alkyl substituted with one to two cyano, examples of cyanoalkyl include cyanomethyl, 1-cyanoethyl, 2-cyanoethyl, 1,1-dicyanoethyl, 1,2-dicyano-n-propyl, 3-cyano-n-propyl, and the like.

The term "alkoxycarbonyl" herein used means the carbonyl substituted with the above-mentioned "alkoxy", examples of alkoxycarbonyl include methoxycarbonyl, ethoxycarbonyl, n-propoxycarbonyl, isopropoxycarbonyl, n-butoxycarbonyl, isobutoxycarbonyl, tert-butoxycarbonyl and the like. Especially, methoxycarbonyl and ethoxycarbonyl are preferred.

BEST MODE FOR CARRYING OUT THE INVENTION

The preparation of the compound of the formula (I) is explained as follows.

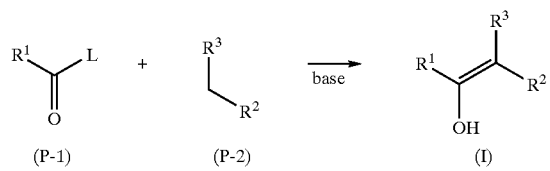

wherein $R^1$ is an optionally substituted carbocyclic group or an optionally substituted heterocyclic group; $R^2$ and $R^3$ taken together with the adjacent carbon atom form an optionally substituted heterocyclic group having one or more of oxo and/or thioxo; L is leaving group (e.g., alkoxy, halogen).

In the above preparation, the compound of the formula (I) is obtained by reacting the compound of the formula (P-1) with the compound of the formula (P-2) in the presence of a base.

Examples of the compound of the formula (P-1) include (substitute(d)benzoic acid ester (e.g., benzoic acid methyl ester, benzoic acid ethyl ester, o-hydroxybenzoic acid methyl ester, o-hydroxybenzoic acid ethyl ester, m-chlorobenzoic acid methyl ester, p-methylbenzoic acid ethyl ester), (substituted)cycloalkanecarboxylic acid ester (e.g., cyclopropanecarboxylic acid ethyl ester, cyclobutanecarboxylic acid ethyl ester, cyclohexanecarboxylic acid ethyl ester, 4-carboxycyclohexanecarboxylic acid ethyl ester, (substituted)cycloalkenecarboxylic acid ester (e.g., 1-cyclohexene-1-carboxylic acid ethyl ester, 4-chloro-1-cyclohexene-1-carboxylic acid ethyl ester), (substituted) heteroarylcarboxylic acid ester (e.g., 5-methyloxazole-2-carboxylic acid ethyl ester, oxazole-2-carboxylic acid ethyl ester, furan-2-carboxylic acid ethyl ester, triazole-3-carboxylic acid ethyl ester, 5-methylisoxazole-3-carboxylic acid ethyl ester, isoxazole-3-carboxylic acid ethyl ester, 5-methyloxadiazole-2-carboxylic acid ethyl ester, tetrazole-5-carboxylic acid ethyl ester, thiophene-2-carboxylic acid ethyl ester, 5-methylfuran-2-carboxylic acid ethyl ester, benzofuran-2-carboxylic acid ethyl ester, furan-3-carboxylic acid ethyl ester, thiophene-3-carboxylic acid ethyl ester, 4-methylisoxazole-5-carboxylic acid ethyl ester, isoxazole-5-carboxylic acid ethyl ester, 5-bromofuran-2-carboxylic acid ethyl ester, pyrrole-2-carboxylic acid ethyl ester, 1-methylimidazole-2-carboxylic acid ethyl ester, 2-trityltriazole-5-carboxylic acid ethyl ester), (substituted) non-aromatic heterocyclecarboxylic acid ester (e.g., morpholine-2-carboxylic acid ethyl ester), (substituted) benzoyl halide (e.g., benzoyl chloride, benzoyl bromide, o-hydroxybenzoyl chloride, o-hydroxybenzoyl bromide, m-chlorobenzoyl chloride, p-methylbenzoyl chloride), (substituted)cycloalkanecarbonyl halide (e.g., cyclopropanecarbonyl chloride, cyclobutanecarbonyl chloride, cyclohexanecarbonyl chloride, 4-carboxycyclohexanecarbonyl chloride), (substituted)cycloalkenecarbonyl halide (e.g., 1-cyclohexene-1-carbonyl chloride, 4-chloro-1-cyclohexene-1-carbonyl chloride), (substituted) heteroarylcarbonyl chloride (e.g., 5-methyloxazole-2-carbonyl chloride, oxazole-2-carbonyl chloride, furan-2-carboxylic acid ethyl ester, triazole-3-carbonyl chloride, 5-methylisoxazole-3-carbonyl chloride, isoxazole-3-carbonyl chloride, 5-methyloxadiazole-2-carbonyl chloride, tetrazole-5-carbonyl chloride, thiophene-2-carbonyl chloride, 5-methylfuran-2-carbonyl chloride, benzofuran-2-carbonyl chloride, furan-3-carbonyl chloride, thiophene-3-carbonyl chloride, 4-methylisoxazole-5-carbonyl chloride, isoxazole-5-carbonyl chloride, 5-bromofuran-2-carbonyl chloride, pyrrole-2-carbonyl chloride, 1-methylimidazole-2-carbonyl chloride, 2-trityltriazole-5-carbonyl chloride), (substituted)non-aromatic heterocyclecarbonyl halide (e.g., morpholine-2-carbonyl chloride).

Examples of the compound of the formula (P-2) include the formula:

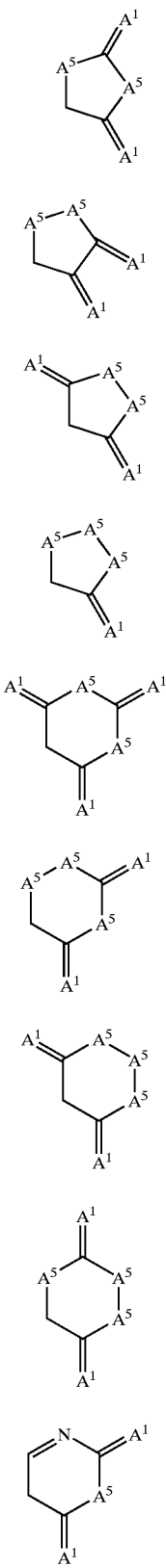

(A')
(B')
(C')
(D')
(E')
(F')
(G')
(H')
(J')

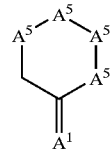

(K')

wherein $A^1$ is each independently oxygen atom or sulfur atom; $A^5$ is each independently —O—, —S—, —NR$^4$— wherein R$^4$ is hydrogen, optionally substituted alkyl, optionally substituted acyl, optionally substituted aryl, or optionally substituted aralkyl, or —CH$_2$—; provided that one or more of $A^5$ is —O—, —S—, or —NR$^4$— wherein R$^4$ is hydrogen, optionally substituted alkyl, optionally substituted acyl, optionally substituted aryl, or optionally substituted aralkyl. More concrete examples are rhodanine, 3-pyridazinone, pyrazolone, 2-methylpyridone, 2-imidazolidinethione, 2-imidazolidone, 3-indolinone, barbituric acid, and the like.

As a base, can be used sodium alcoholate (e.g., sodium methylate, sodium ethylate), n-butyl lithium, LDA (lithium diisopropylamide), sodium hydride, LHMDS (lithium bis(trimethylsilyl)amide) or the like. Especially, n-butyl lithium, LDA and LHMDS are preferred. The base may be selected depending on the kind of substitutent(s) on the group represented by the formula R$^1$ in the compound of the formula (P-2) or the characteristic of the compound of the formula (P-2).

In the present preparation, it is preferred to react at a low temperature depending on the kind of base, for example, at −10 to 0° C. For example, when as a base used is n-butyl lithium, LDA, or LHMDS, it is preferred to react at −80 to −60° C.

Furthermore, the above reaction may be conducted as that to the compound of the formula (P-2) is added a base at low temperature (e.g., −80 to −60° C.), and the reaction mixture is stirred at the same temperature for several minutes to several hours, followed by warming to 0° C. to room temperature, then cooled again, and to the reaction mixture is added the compound of the formula (P-1).

In the above-mentioned reaction, the substitutent(s) on the group represented by the formula R$^1$ of the compound of the formula (P-1) may be protected and deprotected if necessary.

Furthermore, the substituent(s) of a group represented by R$^1$ of the compound of the formula (P-1) can be introduced thereto before or after the above-mentioned reaction. Especially, when the group represented by the formula: —R$^1$ is an aromatic group, the introduction of substituent is easy. For example, an aromatic compound substituted with nitro can be obtained by nitration using mixed acid or the like. Moreover, an aromatic compound substituted with amino can be obtained by reduction using tin or the like in hydrochloric acid. Moreover, an aromatic compound substituted with hydroxy can be obtained by diazotization followed by basic solvolysis. Furthermore, an aromatic compound substituted with alkoxy can be obtained by reacting a diazo derivative with an alcohol. Furthermore, an aromatic compound substituted with halogen can be obtained by Sandmeyer reaction, i.e. reaction of a diazo derivative with a copper(II) salt (e.g., CuCl$_2$, CuBr$_2$). Moreover, an aromatic compound substituted with halogen can be obtained too by direct chlorination or the like. Halogen can be introduced into a desired position by using these methods.

Alkyl, alkenyl and acyl can be directly introduced to an aromatic group by Friedel-Crafts reaction using anhydrous aluminium chloride and the like, and an alkylation reagent, alkenylation reagent, or acylation reagent.

Compounds used in the present invention include regioisomers thereof. Regioisomer means a cis or trans isomer of the compound of the formula (I) or (II). Furthermore, the present invention includes tautomers thereof. Tautomer means a keto tautomer or enol tautomer of the compound of the formula (I) or (II). For example, the regioisomer and tautomer of the compound of the formula (I) or (II) are described as follows.

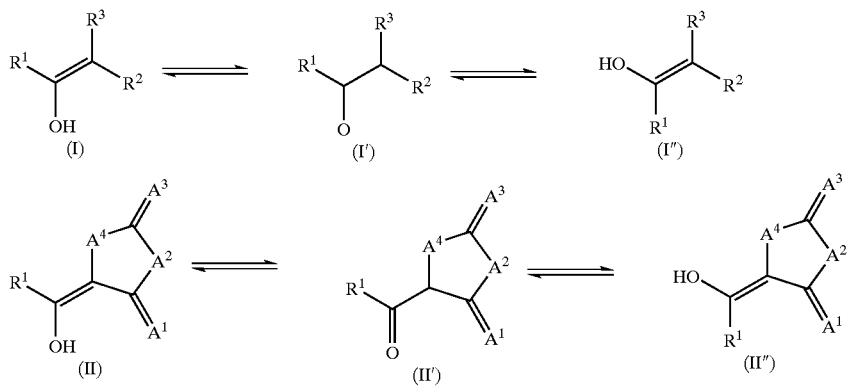

wherein each symbol is as defined above.

Furthermore, the compound of the formula (I') and (II') of the present invention include R-form and S-form described below.

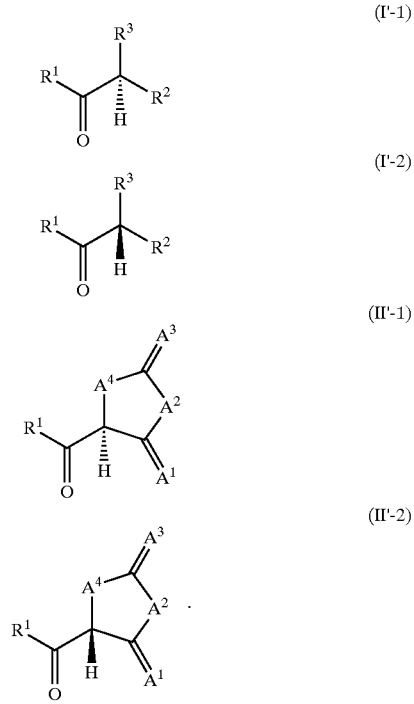

Moreover, most of NMR data are described as corresponding to the structure of the above-mentioned the formula (I) or (II), depending on the measuring condition in later-mentioned examples.

Prodrug is included in the compound of the present invention. Prodrug is a derivative of the compound having a group which can be decomposed chemically or metabolically, and such a prodrug is a compound according to the present invention which becomes pharmaceutically active by solvolysis or under a physiological condition in vivo. The method of selection and manufacture of appropriate prodrug derivatives is described in, for example. Design of Prodrugs, Elsevier, Amsterdam, 1985.

The present invention relates to a treating agent against hepatitis C virus, thus preferable is a prodrug for transferring to liver as a target. The prodrug for transferring to liver is preferably that having higher lipophilicity, which can be achieved by modifying carboxyl, hydroxy, or amino of a compound.

For example, in case of the compound of the formula (I) or (II) having carboxy, examplified is an ester derivative which is prepared by reacting an acidic compound and a suitable alcohol. Especially preferable ester derivatives as prodrug are alkyl ester (e.g., methyl ester, ethyl ester, n-propyl ester, isoprpyl ester, n-butyl ester, isobutyl ester, tert-butyl ester, benzyl ester) having 1 to 30 carbon atom(s) optionally substituted with one or more substituent(s) selected from a group consisted of carboxy, dimethylamino, alkylcarbonyloxy (e.g., —OCO($CH_3$)$_3$), alkyloxycarbonyloxy (e.g., —OCOO$C_2H_5$), and aryl.

Furthermore, in case of the compound of the formula (I) or (II) having hydroxy, examplified is an acyloxy derivative which is prepared by reacting a compound having hydroxy and a suitable acyl halide or suitable acid anhydride. Especially preferable acyloxy derivatives as prodrug are alkylcarbonyloxy (e.g., —OCO$C_2H_5$, —OCO(tert-Bu), —OCO$C_{15}H_{31}$, —OCO$CH_2CH_2$COONa, —OCOCH($NH_2$)$CH_3$, —OCO$CH_2$N($CH_3$)$_2$ having 1 to 30 carbon atom(s) optionally substituted with one or more substituent(s) selected from a group consisted of COONa, COOK, amino, carboxy, and dimethylamino, arylcarbonyloxy (e.g., —OCOPh(2-COONa)) optionally substituted with COONa, and the like.

Furthermore, in case of the compound of the formula (I) or (II) having amino, examplified is an amide derivative which is prepared by reacting a compound having amino and a suitable acyl halide or suitable mixed acid anhydride. Especially preferable amide derivatives as prodrug are alkylcarbonylamino (e.g., —NHCO($CH_2$)$_{20}CH_3$, —NHCOCH($NH_2$)$CH_3$) having 1 to 30 carbon atom(s) optionally substituted with amino.

Examples of the compound of the formula (I) or (II) or a prodrug thereof include alkali metal salt (e.g., lithium salt, sodium salt, potassium salt,), alkaline-earth metal salt (e.g., calcium salt), salt of organic base (e.g., tromethamine, trimethylamine, triethylamine, 2-aminobutane, tert-butylamine, diisopropylethylamine, n-butylmethylamine, cyclohexylamine, N-isopropylcyclohexylamine, furfurylamine, benzylamine, methylbenzylamine, dibenzylamine, N,N-methylbenzylamine, 2-chlorobenzylamine, 4-methoxybenzylamine, 1-naphthylenemethylamine, diphenylbenzylamine, triphenylamine, 1-naphtylamine, 1-aminoanthracene, 2-aminoanthracene, dehydroabiethylamine, N-methylmorpholine, or pyridine), or amino acid salt (e.g., lysine salt, arginine salt).

For example, the compound of the formula (II) in the present invention can be in the following structure:

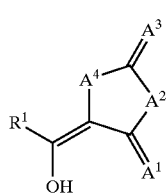
(II)

wherein $A^1$ is oxygen atom; $A^2$ is —NH—; other symbols are as defined above.

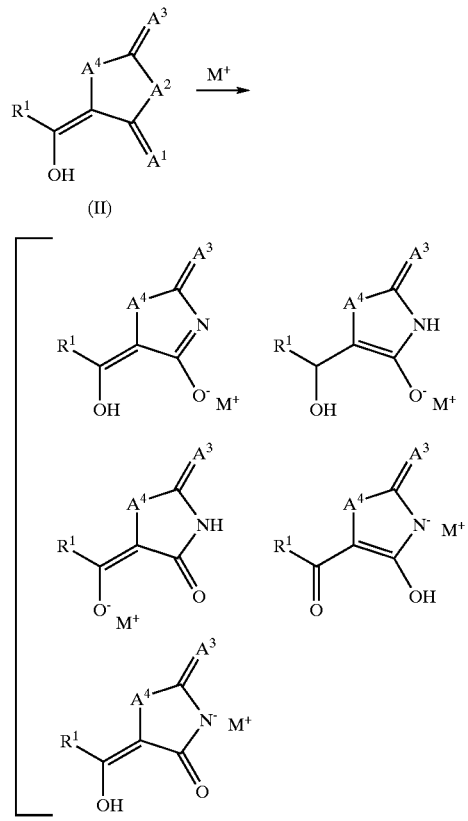

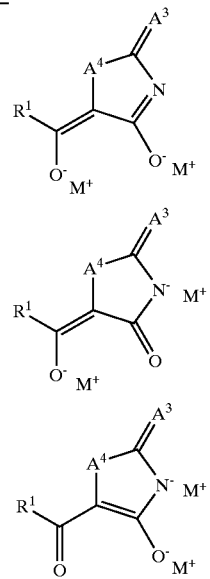

wherein $A^1$ is oxygen atom; $A^2$ is —NH—; other symbols are as defined above; $M^+$ is a metal ion, e.g., $Li^+$, $Na^+$, $K^+$, $½Ca^{2+}$, $NH_4^+$.

The term "solvate" used herein means a solvate of the compound of the formula (I) or (II), a tautomer, a prodrug, or a pharmaceutical acceptable salt thereof, for example, including solvates with alcohol (e.g., ethanol), hydrates, and the like. As hydrates exampled are monohydrate, dihydrate, and the like.

The compounds of the formula (I) or (II) have an inhibitory activity against nucleic acid polymerase, especially, against nucleic acid polymerase of virus. The structure of nucleic acid polymerase is different depending on virus, however, in WO 00/06528, WO 98/41196, and the like it is described that various nucleic acid polymerase have a common function, thus inhibitors thereof can be used commonly. For example, a compound having an inhibitory activity against nucleic acid polymerase of a certain virus has an inhibitory activity against nucleic acid polymerase of other virus. A compound of the present invention has not only an inhibitory activity against a HCV RNA-dependent RNA polymerase, but also an inhibitory activity against a BVDV RNA-dependent RNA polymerase, thus which can be used as an inhibitor against several nucleic acid polymerase.

Especially, the compound of the present invention is usuful as RNA-dependent RNA polymerase inhibitor. Therefore, a compound of the present invention can be used for treating diseases related to virus having RNA-dependent RNA polymerase. Such viruses include that belonging to the family Flaviviridae (e.g., hepatitis C virus (HCV), dengue virus, Japanese encephalitis virus), virus belonged the family Togaviridae (e.g., Sindbis virus, bovine virus diarrhea virus (BVDV; bovine virus diarrhea virus)). Therefore, a pharmaceutical composition containing the compound of the formula (I) or (II) is useful as an anti-flavivirus agent and anti-togavirus agent. Furthermore, the compound of the formula (I) or (II) has a strong inhibitory effect especially against HCV RNA-dependent RNA polymerase, and a pharmaceutical composition containing the compound can be an effective anti-HCV agent or treating agent against hepatitis C.

The compound used in the present invention can be administered orally or parenterally. In case of oral administration, a compound used in the present invention can be used as any one of usual medication, for example, solid medicine such as tablet, powder, granule, capsule; solution; oily suspending agent; or syrup agent, or liquid medicine such as elixir agent. In case of parenteral administration, a compound used in the present invention can be used as aqueous or oily suspension parenteral injection, nasal drop. In the preparation of them, can be used optionally, usual vehicle, binding agent, lubricant, aqueous solvent, oilness solvent, emulsifier, suspending agent, preservatives, stabilizer, and the like.

The medication of the compound used in the present invention is prepared by combining (e.g., mixing) an therapeutically effective dose of the compound with a pharmaceutically acceptable carrier or diluent. The medication of a compound used in the present invention is prepared by known methods using well-known, easily obtainable components.

In case of manufacturing a pharmaceutical composition of the compound used in the present invention, active ingredients are admixed or diluted with a carrier, or they are contained in a carrier in the form of capsule, sacheier, paper, or another container. In case of functioning a carrier as a diluent, the carrier is a solid, semi-solid, or liquid material which functions as a medium, and they may be formulated to tablet, pill, powder medicine, intraoral medicine, elixir agent, suspending agent, emulsifier, dissolving agent, syrup agent, aerosol agent (solid in liquid medium), and ointment. Such a formulation may contain up to 10% of an active compound. It is preferred to prepare a formulation of compounds used in the present invention prior to administration.

Any suitable carrier well known by those skilled in the art may be used for the formulation. In such a formulation, a carrier is in the form of solid, liquid, or a mixture thereof. For instance, the compound of the present invention is dissolved into 4% dextrose/0.5% sodium citrate aqueous solution so as to be 2 mg/mL concentration for intravenous injection. Solid formulation includes powder, tablet, and capsule. Solid carrier consists of one or more of material(s) for serving also as fragrant, lubricant, dissolving agent, suspension, binder, tablet disintegrator, capsule. A tablet for oral administration contains a disintegrator such as corn starch, alginic acid and the like, and/or a binder such as gelatin, acacia and the like, and a lubricant such as magnesium stearate, stearic acid, talc and the like, and a suitable excipient such as calcium carbonate, sodium carbonate, lactose, calcium phosphate.

In a powder medicine, a carrier is a finely pulverized solid which is blended with finely pulverized active ingredients. In a tablet, active ingredients are admixed with a carrier having required binding power in a suitable ratio, and it is solidified in a desired shape and size. Powder medicine and tablet contain about 1 to about 99% by weight of the active ingredients being novel compounds according to the present invention. Examples of suitable solid carriers include magnesium carbonate, magnesium stearate, talc, sugar, lactose, pectin, dextrin, starch, gelatin, tragacanth gum, methyl cellulose, sodium carboxymethylcellulose, low-melting wax, and cocoa butter.

An axenic liquid formulation contains suspending agent, emulsifier, syrup agent, and elixir agent. Active ingredients may be dissolved or suspended into a pharmaceutically acceptable carrier such as sterile water, a sterile organic solvent, a mixture thereof and the like. Active ingredients may be dissolved frequently into a suitable organic solvent such as propylene glycol aqueous solution. When finely pulverized active ingredients are dispersed into aqueous starch, sodium carboxylmethylcellulose solution, or suitable oil, the other compositions can be prepared.

The dosage varies with the conditions of the disease, administration route, age and body weight of patient. In case of oral administration, the dosage can generally be between 0.05 to 3000 mg/kg/day, preferably 0.1 to 1000 mg/kg/day for an adult, which is provided in divisions if necessary. Furthermore, in case of parenteral administration, the dosage can generally be between 0.01 to 1000 mg/kg/day, preferably 0.05 to 500 mg/kg/day. for an adult.

Furthermore, the pharmaceutical composition of the present invention may include another treating agent against hepatitis C (e.g., interferon, protease inhibitor, nucleic acid polymerase inhibitor, immunoactivable agent,). Especially, such a treating agent preferably is that having a different effect mechanism, producing a synergistic effect with the compound of the present invention, from that of an agent of the present invention (e.g., protease inhibitor) is preferred.

Moreover, the present invention includes a treating method against hepatitis C characterized by administrating a treating agent against hepatitis C containing the compound of the present invention and use of the compound of the present invention for preparing a treating agent against hepatitis C.

EXAMPLE

The following examples are provided to further illustrate the present invention and are not to be construed as limiting the scope thereof. Abbreviations described below are used in the following examples.

Me methyl; Et: ethyl; LHMDS: lithium bis(trimethylsilyl)amide; THF tetrahydrofuran; n-BuLi: n-butyllithium Example 1

5-[1-Hydroxy-1-(5-methyloxazol-2-yl)]methylene-2-thioxothiazolidin-4-one (Compound I-1)

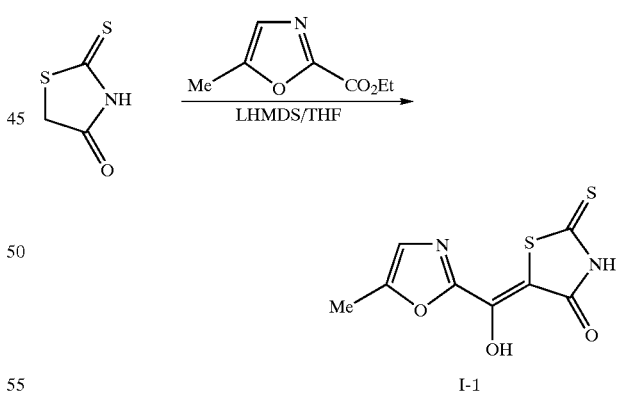

To a solution of rhodanine (0.266 g, 2 mmol) in THF (10 mL) was added dropwise a n-hexane solution of lithium bis(trimethylsilyl)amide (1 M, 4 mL, 4 mmol) at −78° C. After the reaction mixture was stirred at the same temperature for 30 min, a solution of 5-methyloxazole-2-carboxylic acid ethyl ester (0.26 g, 1.7 mmol) in THF (5 mL) was added thereto. The reaction mixture was stirred at −78° C. for 1 h and at 0° C. for 2 h, and adjusted to pH 3 by addition of 10% aqueous solution of citric acid. The resulting solid was filtered, washed with water and ethyl acetate successively, and was suspended into 2 mol/L, hydrochloric acid. To the suspension was added ethyl acetate and the solution was extracted two times with ethyl acetate. The extract was washed with water and brine successively, treated with active carbon, and dried. The solvent was evaporated, and the obtained crystals were filtered and washed with n-hexane/ethyl acetate=3/1 (v/v) to give the title compound (0.21 g).

m.p.: 243–245° C. (decomposition) Anal. Calcd for $C_8H_6N_2O_3S_2$: C, 39.66; H, 2.50; N, 11.56; S, 26.47. Found: C, 39.81; H, 2.54; N, 11.25; S, 26.51. NMR($d_6$-DMSO) δ: 2.43(3H, d, J=1.8 Hz), 7.34(1H, d, J=1.8 Hz).

Example 2

5-[1-(Furan-2-yl)-1-hydroxy]methylene-2-thioxothiazolidin-4-one (Compound I-2)

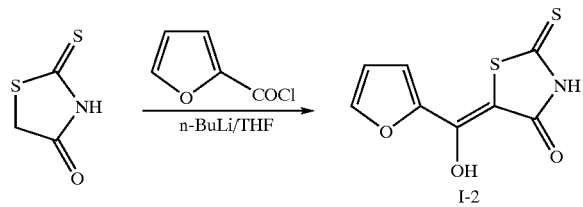

To a solution of rhodanine (0.615 g, 4.6 mmol) in THF (10 mL) was added dropwise a n-hexane solution of n-butyl lithium (1.5 M, 6.2 mL, 9.3 mmol) at −78° C. for 15 min. After the reaction mixture was stirred at the same temperature for 15 min and warmed gradually to 0° C., and then stirred for additional 30 min. The reaction mixture was cooled to −78° C. again and a solution of 2-furoyl chloride (0.66 g, 5.1 mmol) in THF (5 mL) was added thereto. The reaction mixture was stirred at same temperature for 30 min and at room temperature for 1 h, adjusted to pH 3 by addition of 2 mol/L hydrochloric acid, and extracted with ethyl acetate. The extract was dried and concentrated, and the residue was partitioned between ethyl acetate and aqueous solution of sodium hydrogen carbonate and stirred for 30 min. The obtained sodium salt was filtered, washed with water and ethyl acetate successively, and suspended into excess of 2 mol/l, hydrochloric acid. The suspension was stirred for 30 min, extracted with ethyl acetate, and dried. The solvent was evaporated, and the obtained crystals were filtered and washed with n-hexane/ethyl acetate (v/v, 3/1) to give the title compound (0.18 g).

m.p.: 230–235° C. (decomposition) Anal. Calcd for $C_8H_5NO_3S_2$ 0.125 $C_4H_8O_2$: C, 42.84; H, 2.54; N, 5.88; S, 26.92. Found: C, 42.61; H, 2.44; N, 5.90; S, 26.64. NMR ($d_6$-DMSO) δ: 6.61(1H, dd, J=3.3, 1.2 Hz), 7.24(1H, d, J=3.3 Hz), 7.94(1H, d, J=1.2 Hz), 13.3(1H, brs).

The following compounds were synthesized in similar manners described above.

Example 3

5-[-Hydroxy-1-(thophen-2-yl)]methylene-2-thioxothiazolidin-4-one (Compound I-3)

m.p.: 213–220° C. (decomposition) Anal. Calcd for $C_8H_5NO_2S_3$: C, 39.49; H, 2.07; N, 5.76; S, 39.53. Found: C, 39.54; H, 2.08; N, 5.80; S, 39.31. NMR($d_6$-DMSO) enol-type/keto-type=7/1 Enol-type δ: 7.24–7.40(1H, m), 7.93 (1H, brs), 8.02(1H, brs). Keto-type δ: 6.58(1H, brs), 7.24–7.40(11H, m), 8.14(1H, brs), 8.22(1H, brs).

Example 4

5-[1-Hydroxy-1-(thiophen-2-yl)]methylenethiazolidine-2,4-dione (Compound I-4)

m.p.: 203–204° C. (decomposition) recrystallization solvent: n-hexane/ethyl acetate Anal. Calcd for $C_8H_5NO_3S_2$: C, 42.28; H, 2.22; N, 6.16; S, 28.22. Found: C, 42.35; H, 2.35; N, 6.16; S, 28.11. NMR($d_6$-DMSO) enol-type/keto-type=1/1 Enol-type δ: 7.28–7.38(1H, m), 7.67(1H, brs), 8.17–8.25 (1H, m). Keto-type δ: 6.47(1H, s), 7.28–7.38(1H, m), 8.05 (1H, d, J=4.2 Hz),8.17–8.25(1H, m).

Example 5

5-[1-Hydroxy-1-(thiophen-2-yl)]methylenethiazolidine-2,4-dione sodium salt (Compound I-5)

m.p.: 205–207° C. (decomposition) recrystallization solvent: ethanol Anal. Calcd for $C_8H_4NO_3S_2Na$ 1.25$H_2O$: C, 35.37; H, 2.41; N, 5.16; Na, 8.46, S, 23.64. Found: C, 35.21; H, 1.85; N, 5.14; Na, 5.70, S, 23.44. NMR($d_6$-DMSO) enol-type/keto-type=1/1 Enol-type δ: 7.28–7.38(1H, m), 7.69(1H, brs), 8.17–8.24(1H, m). Keto-type δ: 6.48(1H, s), 7.28–7.38(1H, m), 8.04(1H, brs), 8.17–8.24(1H, m).

Example 6

5-[1-Hydroxy-1-(3-methoxyphenyl)]methylenethiazolidine-2,4-dione (Compound I-6)

m.p.: 159–160° C. recrystallization solvent: methanol Anal. Calcd for $C_{11}H_9NO_4S$: C, 52.58; H, 3.61; N, 5.57, S, 12.76. Found: C, 52.47; H, 3.39; N, 5.64; S, 12.68. NMR ($d_6$-DMSO) enol-type/keto-type=2/1 Enol-type δ: 3.81(3H, s), 7.00–7.40(4H, m). Keto-type δ: 3.84(3H, s), 6.63(1H, s), 7.00–7.70(4H, m).

Example 7

5-[1-Hydroxy-1-(3-hydroxyphenyl)]methylenethiazolidine-2,4-dione (Compound I-7)

m.p.: 237–239° C. (decomposition) recrystallization solvent: ethyl acetate Anal. Calcd for $C_{10}H_7NO_4S$: C, 50.63; H, 2.97; N, 5.90, S, 13.52. Found: C, 52.33; H, 3.04; N, 5.88; S, 13.60. NMR($d_6$-DMSO) enol-type/keto-type=4/1 Enol-type δ: 6.80–7.50(4H, m), 10.0(1H, brs). Keto-type δ: 6.51 (1H, s), 6.80–7.50(4H, m), 9.68(1H, brs).

Example 8

5-[1-Hydroxy-1-(thiophen-3-yl)]methylenethiazolidine-2,4-dione (Compound I-8)

m.p.: 214–216° C. (decomposition) Anal. Calcd for $C_8H_5NO_3S_2$: C, 42.28; H. 2.22; N, 6.16; S, 28.22. Found: C, 42.21; H, 2.27; N, 6.19; S, 27.94. NMR($d_6$-DMSO) enol-type/keto-type=2/1 Enol-type δ: 7.44(1H, d, J=4.5 Hz), 7.79(1H, brs), 8.17(1H, brs). Keto-type δ: 6.42(1H, s), 7.58(1H, dd, J=1.8, 4.5 Hz), 7.73(1H, d, J=4.5 Hz), 8.74(1H, d, J=1.8 Hz).

Example 9

5-[1-(Furan-2-yl)-1-hydroxy]methylenethiazolidine-2,4-dione (Compound I-9)

m.p.: 141–142° C. recrystallization solvent: diisopropyl ether Anal. Calcd for $C_8H_5NO_4S$ 0.25$C_6H_{14}O$ 0.125$H_2O$: C, 47.74; H, 3.69; N, 5.86; S, 13.42. Found: C, 47.76; H, 3.49; N, 5.80; S, 13.54. NMR($d_6$-DMSO) enol-type/keto-type= 7/1 Enol-type δ: 6.70–8.40(3H, m), 12.7(1H, brs). Keto-type δ: 6.21(1H, s), 6.70–8.40(3H, m), 12.5(1H, brs).

Example 10

5-[1-Hydroxy-1-(thiophen-2-yl)]methylene-3-methylthiazolidine-2,4-dione (Compound I-10)

m.p.: 153–154° C. recrystallization solvent: n-hexane/ethyl acetate Anal. Calcd for $C_9H_7NO_3S_2$ $0.125H_2O$: C, 44.35; H, 3.00; N, 5.75; S, 26.31. Found: C, 44.69; H, 2.78; N, 5.86; S, 26.31. NMR($d_6$-DMSO) enol-type/keto-type= 1/1 Enol-type δ: 3.00(3H, s), 7.27–7.40(1H, m), 7.70(1H, brs), 8.20–8.26(1H, m). Keto-type δ: 3.10(3H, s), 6.49(1H, s), 7.27–7.40(1H, m), 8.06(1H, brs), 8.20–8.26(1H, m).

Example 11

5-[1-Hydroxy-1-(2-me thoxyphenyl)]methylene-2-thioxo thiazolidin-4-one (Compound I-11)

m.p.: 183–185° C. (decomposition) recrystallization solvent: diisopropyl ether Anal. Calcd for $C_{11}H_9NO_3S_2$: C, 49.42; H, 3.39; N, 5.24, S, 23.99. Found: C, 49.46; H, 3.51; N, 5.16; S, 23.71. NMR($d_6$-DMSO) δ: 3.78(3H, s), 7.00(1H, t, J=8.4 Hz), 7.12(1H, d, J=8.4 Hz), 7.34(1H, d, J=6.3 Hz), 7.46–7.52(1H, m).

Example 12

5-[1-Hydroxy-1-(2-methoxyphenyl)]methylenethiazolidine-2,4-dione (Compound I-12)

m.p.: 143–146° C. recrystallization solvent: diisopropyl ether Anal. Calcd for $C_{11}H_9NO_4S$: C, 52.58; H, 3.61; N, 5.57, S, 12.76. Found: C, 52.52; H, 3.59; N, 5.55; S, 13.04. NMR($d_6$-DMSO) enol-type/keto-type=4/1 Enol-type δ: 3.77 (3H, s), 6.92–7.70(4H, m). Keto-type δ: 3.86(3H, s), 6.00 (1H, s), 6.92–7.70(4H, m).

Example 13

5-[1-(Benzofuran-2-yl)-1-hydroxy]methylenethiazolidine-2,4-dione (Compound I-13)

m.p.: 275–278° C. (decomposition) recrystallization solvent: n-hexane/ethyl acetate Anal. Calcd for $C_{12}H_7NO_4S$ $0.125H_2O$: C, 54.69; H, 2.87; N, 5.32, S, 12.17. Found: C, 54.68; H, 2.49; N, 5.37; S, 12.18. NMR($d_6$-DMSO) enol-type/keto-type=7/1 Enol-type δ: 7.34–8.22(5H, m). Keto-type δ: 6.45(1H, s), 7.34–8.22(5H, m).

Example 14

5-[1-(Benzofuran-2-yl)-1-hydroxy]methylene-2-thioxothiazolidin-4-one (Compound I-14)

m.p.: 235–240° C. (decomposition) recrystallization solvent: n-hexane/ethyl acetate Anal. Calcd for $C_{12}H_7NO_3S_2$: C, 51.97; H, 2.54; N, 5.05, S, 23.12. Found: C, 51.98; H, 2.54; N, 4.89; S, 22.21. NMR($d_6$-DMSO) δ: 7.30–7.84(5H, m), 7.95(1H, brs), 13.5(1H, brs).

Example 15

3-Carboxymethyl-5-[1-(furan-2-yl)-1-hydroxy]methylene-2-thioxothiazolidin-4-one (Compound I-15)

m.p.: 237–240° C. (decomposition) recrystallization solvent: n-hexane/ethyl acetate Anal. Calcd for $C_{10}H_7NO_5S_2$: C, 42.10; H. 2.47; N, 4.91, S, 22.48. Found: C, 42.19; H, 2.57; N, 4.82; S, 22.03. NMR($d_6$-DMSO) δ: 4.67(2H, s), 6.78(1HT, brs), 7.80(1H, brs), 8.07(1H, brs).

Example 16

3-Carboxymethyl-5-[1-(thiol)hen-2-yl)-1-hydroxy] methylene-2-thioxothiazolidin-4-one (Compound I-16)

m.p.: 215–220° C. (decomposition) recrystallization solvent: diisopropyl ether Anal. Calcd for $C_{10}H_7NO_4S_3$: C, 39.86; H, 2.34; N, 4.65, S, 31.92. Found: C, 39.89; H, 2.43; N, 4.59; S, 31.42. NMR($d_6$-DMSO) δ: 4.66(2H, s), 7.22(1H, brs), 7.87(1H, brs), 8.45(1H, brs).

Example 17

5-[1-Hydroxy-1-(2-hydroxyphenyl)]methylene-2-thioxothiazolidin-4-one (Compound I-17)

m.p.: 178–180° C. (decomposition) recrystallization solvent: n-hexane/diisopropyl ether Anal. Calcd for $C_{10}H_7NO_3S_2$: C, 47.42; H, 2.79; N, 5.53, S, 25.32. Found: C, 47.30; H, 2.88; N, 5.57; S, 24.75. NMR($d_6$-DMSO) δ: 6.80–6.90(2H, m), 7.25–7.35(1H, m), 7.50(1H, brs), 12.0 (1H, brs).

Example 18

5-[1-Hydroxy-1-(2-hydroxyphenyl)]methylenethiazolidine-2,4-dione (Compound I-18)

m.p.: 138–140° C. recrystallization solvent: n-hexane/ether Anal. Calcd for $C_{10}H_7NO_4S$: C, 50.63; H, 2.97; N, 5.90, S, 13.52. Found: C, 50.41; H, 3.00; N, 5.88; S, 13.64. NMR($d_6$-DMSO) Enol-type δ: 6.80–6.90(2H, m), 7.20–7.40 (2H, m), 11.5(1H, brs). Keto-type δ: 6.15(1H, s), 6.90–7.00 (2H, m), 7.50–7.80(2H, m), 11.3(1H, s).

Example 19

5-[1-(Furan-3-yl)-1-hydroxy]methylenethiazolidine-2,4-dione (Compound I-19)

m.p.: 201–204° C. (decomposition) recrystallization solvent: n-hexane/ethyl acetate Anal. Calcd for $C_8H_5NO_4S$ $0.125C_4H_8O_2$: C, 45.94; H, 2.72; N, 6.30; S, 14.43. Found: C, 45.83; H, 2.61; N, 6.49; S, 14.72. NMR($d_6$-DMSO) enol-type/keto-type=3/Enol-type δ: 7.90(2H, brm), 8.35(1H, s). Keto-type δ: 6.16(1H, s), 6.89(1H, brm), 7.90(1H, brm), 8.79(1H, s).

Example 20

5-[1-(Furan-3-yl)-1-hydroxy]methylene-2-thioxothiazolidin-4-one (Compound I-20)

m.p.: 178–180° C. (decomposition) recrystallization solvent: n-hexane/diisopropyl ether Anal. Calcd for $C_8H_5NO_3S_2$ $0.125H_2O$: C, 41.86; H, 2.31; N, 6.10; S, 27.94. Found: C, 41.83; H, 2.36; N, 6.19; S, 27.95. NMR($d_6$-DMSO) δ: 6.88(1H, m), 7.86(1H, m), 8.52(1H, m), 13.3(2H, brs).

Example 21

5-[1-Hydroxy-1-(pyrrol-2-yl)]methylene-2-thioxothiazolidin-4-one (compound I-21)

m.p.: 160–163° C. (decomposition) recrystallization solvent: diisopropyl ether NMR($d_6$-DMSO) δ: 5.30–7.20(3H, m), 12.0(1H, brs), 13.0(1H, brs).

Example 22

5-[1-Hydroxy-1-(5-methylfuran-2-yl)]methylene-2-thioxothiazolidin-4-one (Compound I-22)

m.p.: 195–198° C. (decomposition) recrystallization solvent: n-hexane/ethyl acetate Anal. Calcd for $C_9H_7NO_3S_2$: C, 44.80; H, 2.92; N, 5.80; S, 26.58. Found: C, 44.78; H, 2.90; N, 5.75; S, 26.28. NMR($d_6$-DMSO) δ: 2.41(3H, s), 6.45(1H, d, J=3.0 Hz), 7.48(1H, d, J=3.0 Hz), 13.4(2H, brs).

Example 23

5-[1-(5-Bromofuran-2-yl)-1-hydroxy-]methylene-2-thioxothiazolidin-4-one (Compound I-23)

m.p.: 205–210° C. (decomposition) recrystallization solvent: n-hexane/ethyl acetate Anal. Calcd for $C_8H_4BrNO_3S_2$ $0.1C_4H_8O_2 0.25H_2O$: C, 31.80; H, 1.60; Br, 25.19; N, 4.42; S, 20.22. Found: C, 31.58; H, 1.45; Br, 25.27; N, 4.69; S, 20.39. NMR($d_6$-DMSO) δ: 6.89(1H, d, J=3.6 Hz), 7.68(1H, d, J=3.6 Hz), 13.3 (2H, brs).

Example 24

5-[1-Hydroxy-1-(5-methylfuran-2-yl)]methylenethiazolidine-2,4-dione (Compound I-24)

m.p.: 275–282° C. (decomposition) Anal. Calcd for $C_9H_7NO_4S$ $2.25H_2O$: C, 43.63; H, 3.87; N, 5.65; S, 12.94. Found: C, 43.81; H, 3.03; N, 6.17; S, 12.90. NMR($d_6$-DMSO) enol-type/keto-type=2/1 Enol-type δ: 2.35(3H, s), 6.29(1H, brm), 6.88(1H, m). Keto-type δ: 2.35(3H, s), 6.07(1H, s), 6.94(1H, brm), 8.05(1H, m).

Example 25

5-[(5-Bromofuran-2-yl)-1-hydroxy]methylenethiazolidine-2,4-dione (Compound I-25)

m.p.: 217–220° C. (decomposition) recrystallization solvent: n-hexane/ethyl acetate Anal. Calcd for $C_8H_4BrNO_4S$: C, 33.12; H, 1.39; Br, 27.54; N, 4.83; S, 11.05. Found: C, 33.12; H, 1.41; Br, 27.29; N, 4.86; S, 11.08. NMR($d_6$-DMSO) enol-type/keto-type=2/1 Enol-type δ: 6.93(1H, brs), 7.32(1H, brs). Keto-type δ: 6.20(1H[, s), 7.02(1H, d, J=3.6 Hz), 7.80(1H, d, J=3.6 Hz), 13.5(1H, brs).

Example 25

5-[1-[5-(4-Fluorobenzyl)furan]-2-yl]-1-hydroxy]methylene-2-thioxothiazolidin-4-one (Compound I-25)

m.p.: 172–175° C. (decomposition) recrystallization solvent: n-hexane/diisopropyl ether Anal. Calcd for $C_{15}H_{10}FNO_3S_2$ $0.125H_2O$: C, 53.36; H, 3.06; F, 5.63; N, 4.15; S, 19.00. Found: C, 53.36; H, 3.00; F, 5.60; N, 4.45; S, 19.06. NMR($d_6$-DMSO) δ: 4.13(2H, s), 6.51(1H, d, J=3.6 Hz), 7.12–7.38(4H, m), 7.41(1H, d, J=3.6 Hz).

Example 26

5-[1-Hydroxy-1-(5-methylisoxazol-3-yl)]methylene-2-thioxothiazolidin-4-one (Compound I-26)

m.p.: 210–214° C. (decomposition) recrystallization solvent: n-hexane/ethyl acetate Anal. Calcd for $C_8H_6N_2O_3S_2$ $0.125H_2O$: C, 39.29; H, 2.58; N, 11.46; S, 26.23. Found: C, 39.29; H, 2.25; N, 11.48; S, 25.97. NMR($d_6$-DMSO) δ: 2.49(3H, s), 6.67(1H, s), 13.1(1H, brs).

Example 27

5-[1-Hydroxy-1-(4-methylisoxazol-5-yl)]methylene-2-thioxothiazolidin-4-one (Compound I-27)

m.p.: 230–234° C. (decomposition) recrystallization solvent: n-hexane/ethyl acetate Anal. Calcd for $C_8H_6N_2O_3S_2$: C, 39.66; H, 2.50; N, 11.56; S, 26.47. Found: C, 39.61; H, 2.47; N, 11.58; S, 26.47. NMR($d_6$-DMSO) δ: 2.32(3H, s), 7.33(1H, s), 12.9(1H, brs).

Example 29

5-[1-(Isoxazol-3-yl)1-hydroxy]methylene-2-thioxothiazolidin-4-one (Compound I-29)

m.p.: 210–215° C. (decomposition) recrystallization solvent: n-hexane/ethyl acetate Anal. Calcd for $C_7H_4N_2O_3S_2$ $0.125H_2O$: C, 36.45; H, 1.86; N, 12.15; S, 27.82. Found: C, 36.67; H, 1.77; N, 11.77; S, 27.34. NMR($d_6$-DMSO) δ: 5.87(1H, d, J=1.7 Hz), 8.64(1H, d, J=1.7 Hz).

Example 30

5-[1-(Isoxazol-5-yl)1-hydroxy]methylene-2-thioxothiazolidin-4-one (Compound I-30)

m.p.: 195–202° C. (decomposition) recrystallization solvent: n-hexane/ethyl acetate Anal. Calcd for $C_7H_4N_2O_3S_2$ $0.063C_4H_8O_2$ $0.125H_2O$: C, 36.90; H, 2.03; N, 11.87; S, 27.17. Found: C, 36.95; H., 0.86; N, 11.87; S, 27.16. NMR($d_6$-DMSO) δ: 7.19(1H, d, J=1.8 Hz), 8.46(1H, d, J=1.8 Hz).

Example 31

5-[1-Hydroxy-1-(1-methylimidazol-2-yl)]methylene-2-thioxothiazolidin-4-one (Compound I-31)

m.p.: 265–270° C. (decomposition) recrystallization solvent: methanol Anal. Calcd for $C_8H_7N_3O_2S_2$: C, 39.82; H, 2.92; N, 17.41; S, 26.58. Found: C, 39.70; H, 2.92; N, 17.23; S, 26.35. NMR($d_6$-DMSO) δ: 4.04(3H, s), 7.70(1H, (I, J=1.5 Hz), 7.79(1H, (1, J=1.5 Hz),12.8(1H, brs).

Example 32

5-[1-Hydroxy-1-(2H-tetrazol-5-yl)]methylene-2-thioxothiazolidin-4-one (Compound I-32)

m.p.: 188–193° C. (decomposition) recrystallization solvent: isopropanol/ethyl acetate Anal. Calcd for $C_5H_3N_5O_2S_2$ $0.33C_3H_8O$ $0.75H_2O$: C, 27.43; H, 2.75; N, 26.66; S, 24.41. Found: C, 27.73; H, 2.74; N, 26.21; S, 24.07. NMR($d_6$-DMSO) δ: 5.55(1H, brs), 12.8(1H, brs).

Example 33

5-[1-Hydroxy-1-(1-trityl-1H-1,2,4-triazol-3-yl)]methylene-2-thioxothiazolidin-4-one (Compound I-33)

m.p.: 216–220° C. (decomposition) recrystallization solvent: ethyl acetate/methanol Anal. Calcd for $C_{26}H_{18}N_4O_3S_2$ $1.13H_2O$: C, 61.17; H, 4.16; N, 11.42; S, 13.07. Found: C, 61.07; H, 4.13; N, 11.71; S, 12.83. NMR($d_6$-DMSO) δ: 7.05–7.50(15H, m), 7.91(1H, s).

Example 34

5-[1-Hydroxy-1-(1H-1,2,4-triazol-3-yl)]methylene-2-thioxothiazolidin-4-one (Compound I-34)

m.p.: 285–290° C. (decomposition) recrystallization solvent: ethyl acetate Anal. Calcd for $C_6H_4N_4O_2S_2$ 0.25C$_4$H$_8$O$_2$ 0.63H$_2$O: C, 31.73; H, 2.36; N, 22.77; S, 26.07. Found: C, 31.57; H, 2.00; N, 22.77; S, 26.69. NMR(d$_6$-DMSO) δ: 8.79(1H, brs), 13.7(3H, brm).

Example 35

5-[1-Hydroxy-1-(pyrimidin-2-yl)]methylene-2-thioxothiazolidin-4-one (Compound I-35)

m.p.: >250° C. (decomposition) recrystallization solvent: ethanol Anal. Calcd for C$_8$H$_5$N$_3$O$_2$S$_2$ 0.15H$_2$O: C, 39.71; H, 2.21; N, 17.37; S, 26.50. Found: C, 39.87; H, 1.93; N, 17.22; S, 26.00. NMR(d$_6$-DMSO) δ: 7.36(1H, t, J=4.8 Hz), 8.70 (2H, d, J=4.8 Hz), 11.7 (1H, brs).

Example 36

5-[1-Hydroxy-1-(pyrazin-2-yl)]methylene-2-thioxothiazolidin-4-one (Compound I-36)

m.p.: >250° C. (decomposition) recrystallization solvent: ethanol Anal. Calcd for C$_8$H$_5$N$_3$O$_2$S$_2$: C, 40.16; H, 2.11; N, 17.56; S, 26.80. Found: C, 40.05; H, 2.13; N, 17.35; S, 26.62. NMR(d$_6$-DMSO) δ: 8.85(1H, s), 8.89(1H, s), 9.25 (1H, s).

Example 37

5-[1-Hydroxy-1-(pyridin-2-yl)]methylene-2-thioxothiazolidin-4-one (Compound I-37)

m.p.: >250° C. (decomposition) recrystallization solvent: ethanol Anal. Calcd for C$_9$H$_6$N$_2$O$_2$S$_2$: C, 45.36; H, 2.54; N, 11.76; S, 26.91. Found: C, 45.16; H, 2.72; N, 11.63; S, 26.79. NMR(d$_6$-DMSO) δ: 7.49(1H, t, J=4.5 Hz), 7.93–8.08 (2H, in), 8.66(1H, d, J=4.5 Hz), 12.4(1H, brs).

Example 38

5-[1-Hydroxy-1-(pyridin-3-yl)]methylene-2-thioxothiazolidin-4-one (Compound I-38)

m.p.: >250° C. (decomposition) recrystallization solvent: ethanol Anal. Calcd for C$_9$H$_6$N$_2$O$_2$S$_2$ 0.1H$_2$O: C, 44.86; H, 2.86; N, 11.66; S, 26.77. Found: C, 45.02; H, 2.60; N, 11.67; S, 26.71. NMR(d$_6$-DMSO) δ: 7.91–7.96(1H, in), 8.61(1H, d, J=8.4 Hz), 8.81(1H, d, J=5.7 Hz), 9.14(1H, d, J=1.8 Hz), 12.2(1H, brs).

Example 39

5-[1-Hydroxy-1-(pyridin-3-yl)]methylene-2-thioxothiazolidin-4-one (Compound I-39)

m.p.: >250° C. (decomposition) recrystallization solvent: methanol Anal. Calcd for C$_9$H$_6$N$_2$O$_2$S$_2$ 0.3H$_2$O: C, 44.36; H, 2.73; N, 11.50; S, 26.31. Found: C, 44.20; H, 2.76; N, 11.57; S, 26.74. NMR(d$_6$-DMSO) δ: 8.08(2H, t, J=5.4 Hz), 8.85(2H, d, J=5.4 Hz), 12.1 (1H, brs).

Example 40

5-[1-Hydroxy-1-(5-methyl-1,3,4-oxadiazol-2-yl)]methylene-2-thioxothiazolidin-4-one (Compound I-40)

m.p.: 230–237° C. (decomposition) recrystallization solvent: ethanol Anal. Calcd for C$_7$H$_5$N$_3$O$_3$S$_2$ 0.1C$_6$H$_8$O$_7$: C, 34.77; H, 2.23; N, 16.01; S, 24.43. Found: C, 34.43; H, 2.46; N, 16.47; S, 24.14. NMR(d$_6$-DMSO) δ: 2.55(3H, s), 12.2 (1H, brs).

Example 41

5-[1-Hydroxy-1-(pyrimidin-4-yl)]methylene-2-thioxothiazolidin-4-one (Compound I-41)

m.p.: >250° C. (decomposition) recrystallization solvent: ethanol Anal. Calcd for C$_8$H$_5$N$_3$O$_2$S$_2$: C, 40.16; H, 2.11; N, 17.56; S, 26.80. Found: C, 39.96; H, 2.05; N, 17.35; S, 26.62. NMR(d$_6$-DMSO) δ: 8.06(1H, t, J=5.1 Hz), 9.10(1H, d, J=5.1 Hz), 9.44 (1H, s).

Example 42

5-[1-(5-Fluorophenyloxazol-2-yl)-1-hydroxy]methylene-2-thioxothiazolidin-4-one (Compound I-42)

m.p.: >250° C. (decomposition) recrystallization solvent: methanol Anal. Calcd for C$_{13}$H$_7$FN$_2$O$_3$S$_2$: C, 48.44; H, 2.28; F, 5.29; N, 8.69; S, 19.90. Found: C, 48.34; H, 2.12; F, 5.75; N, 8.59; S, 19.79. NMR(d$_6$-DMSO) δ: 7.39(1H, d, J=9.0 Hz), 7.42(1H, d, J=9.0 Hz), 7.88 (1H, d, J=9.0 Hz), 7.89(1H, d, J=9.0 Hz), 8.09(1H, s).

Example 43

5-[1-Hydroxy-1-(thiazol-2-yl)]methylene-2-thioxothiazolidin-4-one (Compound I-43)

m.p.: 231° C. recrystallization solvent: ethanol Anal. Calcd for C$_7$H$_4$N$_2$O$_2$S$_3$ 0.1C$_2$H$_6$O 0.15H$_2$O: C, 34.37; H, 1.96; N, 11.13; S, 38.22. Found: C, 34.73; H, 1.81; N, 11.26; S, 37.90. NMR(d$_6$-DMSO) δ: 8.13(1H, s), 8.19(1H, s).

Example 44

5-[1-Hydroxy-1-(4-methoxypyridin-2-yl)]methylene-2-thioxothiazolidin-4-one (Compound I-44)

m.p.: >250° C. (decomposition) recrystallization solvent: methanol Anal. Calcd for C$_{10}$H$_8$N$_2$O$_3$S$_2$ 0.1H$_2$O: C, 44.47; H, 3.06; N, 10.37; S, 23.74. Found: C, 44.30; H, 2.88; N, 10.22; S, 23.82. NMR(d$_6$-DMSO) δ: 4.11(3H, s), 7.64(1H, m), 7.87(1H, s), 8.87(1H, d, J=6.6 Hz), 13.0(1H, brs).

Example 45

5-[1-Hydroxy-1-(4-hydroxypyridin-2-yl)]methylene-2-thioxothiazolidin-4-one (Compound I-45)

m.p.: 255° C. recrystallization solvent: methanol Anal. Calcd for C$_9$H$_6$N$_2$O$_3$S$_2$ 0.3CH$_4$O: C, 42.32; H, 2.75; N, 10.62; S, 24.29. Found: C, 42.41; H, 2.57; N, 10.69; S, 24.03. NMR(d$_6$-DMSO) δ: 7.29(1H, dd, J=6.3, 2.7 Hz), 7.65(1H, d, J=2.7 Hz), 8.67(1H, d, J=6.3 Hz).

Example 46

5-[1-(5-Ethoxycarbonylpyrimidin-2-yl)-1-hydroxy]methylene-2-thioxothiazolidin-4-one (Compound I-46)

m.p.: >250° C. (decomposition) recrystallization solvent: methanol Anal. Calcd for C$_{11}$H$_9$N$_3$O$_4$S$_2$C, 42.44; H, 2.91; N, 13.50; S, 20.60. Found: C, 42.63; H, 2.89; N, 13.20; S, 20.52. NMR(d$_6$-DMSO) δ: 1.37(3H, t, J=7.2 Hz), 4.41(2H, q, J=7.2 Hz), 9.44 (2H, s).

Example 47

5-[1-(5-Carboxypyrimidin-2-yl)-1-hydroxy]methylene-2-thioxothiazolidin-4-one (Compound I-47)

m.p.: >250° C. (decomposition) recrystallization solvent: methanol Anal. Calcd for C$_9$H$_5$N$_3$O$_4$S$_2$ 0.3H$_2$O: C, 37.00;

H, 2.04; N, 14.55; S, 22.60. Found: C, 37.33; H, 1.98; N, 14.51; S, 22.14. NMR($d_6$-DMSO) δ: 9.41(2H, s), 13.8(1H, brs).

Example 48

5-[1-Hydroxy-1-(5-methoxypyridin-2-yl)]methylene-2-thioxothiazolidin-4-one (Compound I-48)

m.p.: >250° C. (decomposition) recrystallization solvent: methanol Anal. Calcd for $C_{10}H_8N_2O_3S_2$: C, 44.76; H, 3.01; N, 10.44; S, 23.90. Found: C, 44.63; H, 3.04; N, 10.33; S, 23.97. NMR($d_6$-DMSO) δ: 3.97(3H, s), 7.64(1H, m), 8.10 (1H, d, J=9.0 Hz), 8.54(1H, s).

Example 49

5-[1-Hydroxy-1-(5-hydroxypyridin-2-yl)]methylene-2-thioxothiazolidin-4-one (Compound I-49)

m.p.: >250° C. (decomposition) recrystallization solvent: ethanol Anal. Calcd for $C_9H_6N_2O_3S_2$ $0.2C_2H_6O$ $0.3H_2O$: C, 41.99; H, 2.92; N, 10.42; S, 23.84. Found: C, 41.87; H, 2.63; N, 10.61; S, 23.52. NMR($d_6$-DMSO) δ: 7.41(1H, brm), 8.03(1H, brm), 8.38(1H, s), 11.2 (1H, brs), 13.5(1H, brs).

Example 50

5-[1-Hydroxy-1-(5-methylthiazol-2-yl)]methylene-2-thioxothiazolidin-4-one (Compound I-50)

m.p.: >250° C. (decomposition) recrystallization solvent: ethanol Anal. Calcd for $C_8H_6N_2O_2S_3$ $0.1H_2O$: C, 36.94; H, 2.40; N, 10.77; S, 36.97. Found: C, 37.20; H, 2.37; N, 10.76; S, 37.24. NMR($d_6$-DMSO) δ: 2.57(3H, s), 7.99(1H, s).

Example 51

5-[1-Hydroxy-1-(4-methylthiazol-2-yl)]methylene-2-thioxothiazolidin-4-one (Compound I-51)

m.p.: >250° C. (decomposition) recrystallization solvent: ethanol Anal. Calcd for $C_8H_6N_2O_2S_3$: C, 37.20; H, 2.34; N, 10.84; S, 37.23. Found: C, 37.00; H, 2.28; N, 10.80; S, 37.01. NMR($d_6$-DMSO) δ: 2.51(3H, s), 7.81(1H, s).

Example 52

5-[1-Hydroxy-1-(2-methylthiazol-5-yl)]methylene-2-thioxothiazolidin-4-one (Compound I-52)

m.p.: >250° C. (decomposition) recrystallization solvent: ethanol Anal. Calcd for $C_8H_6N_2O_2S_3$: C, 37.20; H, 2.34; N, 10.84; S, 37.23. Found: C, 37.16; H, 2.39; N, 10.80; S, 37.51. NMR($d_6$-DMSO) δ: 2.77(3H, s), 8.41(1H, s), 13.5 (1H, brs).

Example 53

5-[1-Hydroxy-1-(2-methyloxazol-4-yl)]methylene-2-thioxothiazolidin-4-one (Compound I-53)

m.p.: 224–226° C. (decomposition) recrystallization solvent: ethanol Anal. Calcd for $C_8H_6N_2O_3S_2$: C, 39.66; H, 2.50; N, 11.56; S, 26.47. Found: C, 39.69; H, 2.36; N, 11.51; S, 26.31. NMR($d_6$-DMSO) δ: 2.52(3H, s), 8.86(1H, s), 13.7(1H, brs).

Example 54

5-[1-(5-Chlorothiazol-2-yl)-1-hydroxy]methylene-2-thioxothiazolidin-4-one (Compound I-54)

m.p.: 255–270° C. (decomposition) recrystallization solvent: ethanol Anal. Calcd for $C_7H_3ClN_2O_2S_3$: C, 30.16; H, 1.08; Cl, 12.72; N, 10.05; S, 34.50. Found: C, 30.14; H, 1.12; Cl, 12.45; N, 10.03; S, 34.40. NMR($d_6$-DMSO) δ: 8.27(1H, s).

Example 55

5-[1-[5-(3-Cyanopropyloxy)pyridin-2-yl]-1-hydroxy]methylene-2-thioxothiazolidin-4-one (Compound I-55)

m.p.: 170° C. (decomposition) recrystallization solvent: ethanol Anal. Calcd for $C_{13}H_{11}N_3O_3S_2$ $0.55C_2H_6O$: C, 48.84; H, 4.16; N, 12.12; S, 18.49. Found: C, 48.79; H, 3.63; N, 12.55; S, 17.50. NMR($d_6$-DMSO) δ: 2.52(3H, s), 8.86 (1H, s), 13.7(1H, brs). Mass: M/Z=322(M+H)$^+$, 320(M−H)$^+$.

Example 56

5-[1-Hydroxy-1-(thiophen-3-yl)]methylene-2-thioxothiazolidin-4-one (Compound I-56)

m.p.: 225–230° C. (decomposition) recrystallization solvent: n-hexane/ethyl acetate Anal. Calcd for $C_8H_5NO_2S_3$ $0.25H_2O$: C, 38.77; H, 2.24; N, 5.68; S, 38.82. Found: C, 38.62; H, 2.01; N, 5.68; S, 39.09. NMR($d_6$-DMSO) δ: 7.47(1H, d, J=5.0 Hz), 7.72(1H, dd, J=5.0, 2.6 Hz), 8.30(1H, m).

Example 57

5-[1-Hydroxy-1-(oxazol-2-yl)]methylene-2-thioxothiazolidin-4-one (Compound I-57)

m.p.: 206–208° C. recrystallization solvent: isopropanol Anal. Calcd for $C_7H_4N_2O_3S_2$: C, 36.84; H, 1.77; N, 12.27; S, 28.10. Found: C, 36.65; H, 1.55; N, 12.14; S, 27.80. NMR($d_6$-DMSO) δ: 7.63(1H, s), 8.43(1H, s).

Example 58

5-[1-Hydroxy-1-(1-methyl-1H-1,2,4-triazol-3-yl)]methylene-2-thioxothiazolidin-4-one (Compound I-58)

m.p.: 252–256° C. (decomposition) recrystallization solvent: isopropanol Anal. Calcd for $C_7H_6N_4O_2S_2$ $0.125H_2O$: C, 34.34; H, 2.57; N, 22.89; S, 26.20. Found: C, 34.58; H, 2.52; N, 22.60; S, 25.88. NMR($d_6$-DMSO) δ: 3.99(3H, s), 8.80(1H, s).

Example 59

5-[1-Hydroxy-1-(3-methoxymethyloxyisoxazol-5-yl)]methylene-2-thioxothiazolidin-4-one (Compound I-59)

m.p.: 178–180° C. (decomposition) recrystallization solvent: isopropanol Anal. Calcd for $C_9H_8N_2O_5S_2$: C, 37.50; H, 2.80; N, 9.72; S, 22.24. Found: C, 37.46; H, 2.74; N, 9.60; S, 21.84. NMR($d_6$-DMSO) δ: 3.45(3H, s), 5.33(2H, s), 7.35(1H, s), 12.5(1H,brs).

Example 60

5-[1-Hydroxy-1-(3-methoxyphenyl)]methylene-2-thioxothiazolidin-4-one (Compound I-60)

m.p.: 182–184° C. recrystallization solvent: n-hexane/ethyl acetate Anal. Calcd for $C_{11}H_9NO_3S_2$: C, 49.42; H, 3.39; N, 5.24; S, 23.99. Found: C, 49.23; H, 3.37; N, 5.29; S, 23.82. NMR($d_6$-DMSO) δ: 3.80(3H, s), 6.99–7.40(4H, m).

Example 61

5-[1-Hydroxy-1-(3-hydroxysoxazol-5-yl)]methylene-2-thioxothiazolidin-4-one (Compound I-61)

m.p.: 235–241° C. (decomposition) recrystallization solvent: n-hexane/ethyl acetate Anal. Calcd for $C_7H_4N_2O_4S_2$ $0.5C_4H_8O_2$ $0.125H_2O$: C, 37.20; H, 2.86; N, 9.64; S, 22.07. Found: C, 37.17; H, 2.74; N, 9.68; S, 21.04. NMR($d_6$-DMSO) δ: 7.18(1H, s), 11.3(1H, brs), 12.1(1H, brs).

Example 62

5-[1-[3-(2-Cyanobenzyloxy)isoxazol-5-yl]-1-hydroxy]methylene-2-thioxothiazolidin-4-one (Compound I-62)

m.p.: 255–260° C. (decomposition) recrystallization solvent: ethyl acetate/methanol Anal. Calcd for $C_{15}H_9N_3O_4S_2$ $0.5C_4H_8O_2$ $0.125H_2O$: C, 50.13; H, 2.52; N, 11.69; S, 17.84. Found: C, 50.12; H, 2.52; N, 11.64; S, 17.95. NMR($d_6$-DMSO) δ: 5.47(2H, s), 7.34(1H, s), 7.61(1H, m), 7.78(2H, d, J=4.2 Hz), 7.94(1H, d, J=7.8 Hz).

Example 63

5-[1-(4,5-Dimethyloxazol-2-yl]-1-hydroxy]methylene-2-thioxothiazolidin-4-one (Compound I-63)

m.p.: 256–259° C. (decomposition) recrystallization solvent: isopropanol Anal. Calcd for $C_9H_8N_2O_3S_2$ C, 42.18; H, 3.15; N, 10.93; S, 25.02. Found: C, 42.35; H, 3.20; N, 10.66; S, 24.88. NMR($d_6$-DMSO) δ: 2.16(3H, s), 2.37(3H, s).

Example 64

5-[1-[3-(3-Cyanopropyloxy)isoxazol-5-yl]-1-hydroxy]methylene-2-thioxothiazolidin-4-one (Compound I-64)

m.p.: 197–199° C. recrystallization solvent: isopropanol Anal. Calcd for $C_{11}H_9N_3O_4S_2$: C, 42.44; H, 2.91; N, 13.50; S, 20.60. Found: C, 42.53; H, 2.86; N, 13.23; S, 20.45. NMR($d_6$-DMSO) δ: 2.07(2H, m), 2.66(2H, t, J=7.2 Hz), 4.23(2H, t, J=6.0 Hz), 7.27(1H, s).

Example 65

5-[1-hHdroxy-1-(5-methyloxazol-2-yl)]methylene-3-methyl-2-thioxothilazolidin-4-one (Compound I-65)

m.p.: 192–195° C. (decomposition) recrystallization solvent: isopropanol NMR($d_6$-DMSO) δ: 2.40(3H, s), 3.31(3H, s), 7.24(1H, s).

Example 66

5-[1-[3-(3-Cyanopropyloxy)]phenyl-1-hydroxy]methylene-2-thioxothiazolidin-4-one (Compound I-66)

m.p.: 125–127° C. recrystallization solvent: isopropanol Anal. Calcd for $C_{14}H_{12}N_2O_3S_2$ $0.125H_2O$: C, 51.75; H, 3.83; N, 8.68; S, 19.88. Found: C, 51.88; H, 3.75; N, 8.71; S, 20.05. NMR($d_6$-DMSO) δ: 2.04(2H, m), 2.67(2H, t, J=7.0 Hz), 4.09(2H, t, J=7.0 Hz), 7.14(1H, d, J=7.8 Hz), 7.21(1H, s), 7.22(1H, d, J=7.8 Hz), 7.43(1H, t, J=7.8 Hz).

Example 67

5-[1-[3-(2-Cyanobenzyloxy)]phenyl-1-hydroxy]methylene-2-thioxothiazolidin-4-one (Compound I-67).

m.p.: 174–176° C. recrystallization solvent: isopropanol Anal. Calcd for $C_{18}H_{12}N_2O_3S_2$: C, 58.68; H, 3.28; N, 7.60; S, 17.41. Found: C, 58.62; H, 3.40; N, 7.69; S, 17.01. NMR($d_6$-DMSO) δ: 5.30(2H, s), 7.22(1H, d, J=8.0 Hz), 7.29(1H, d, J=8.0 Hz), 7.35(1H, s), 7.44(1H, t, J=8.0 Hz), 7.59(1H, m), 7.75(1H, m), 7.77(1H, m), 7.93 (1H, d, J=7.8 Hz).

Example 68

5-[1-(5-Ethyloxazol-2-yl)-1-hydroxy]methylene-2-thioxothiazolidin-4-one (Compound I-68)

m.p.: 201–204° C. (decomposition) recrystallization solvent: isopropanol Anal. Calcd for $C_9H_8N_2O_3S_2$ $0.25H_2O$: C, 41.44; H, 3.29; N, 10.74; S, 24.59. Found: C, 41.18; H, 2.98; N, 10.58; S, 24.38. NMR($d_6$-DMSO) δ: 1.23(3H, t, J=7.5 Hz), 2.79(2H, q, J=7.5 Hz), 7.35 (1H, s).

Example 69

5-[1-Hydroxy-1-(5-methoxyoxazol-2-yl)]methylene-2-thioxothiazolidin-4-one (Compound I-69)

m.p.: 191–195° C. (decomposition) recrystallization solvent: isopropanol Anal. Calcd for $C_8H_6N_2O_4S_2$ $0.125H_2O$: C, 36.88; H, 2.42; N, 10.75; S, 24.62. Found: C, 36.68; H, 2.69; N, 10.88; S, 24.73. NMR($d_6$-DMSO) δ: 4.02(3H, s), 6.88(1H, s).

Example 70

5-[1-(5-Ethoxyoxazol-2-yl)-1-hydroxy]methylene-2-thioxothiazolidin-4-one (Compound I-70)

m.p.: 195–198° C. recrystallization solvent: isopropanol Anal. Calcd for $C_9H_8N_2O_4S_2$ $0.17C_3H_8O$ $0.125H_2O$: C, 40.26; H, 2.98; N, 9.89; S, 22.63. Found: C, 40.41; H, 3.20; N, 9.81; S, 22.70. NMR($d_6$-DMSO) δ: 1.38(3H, t, J=6.6 Hz), 4.31(2H, q, J=6.6 Hz), 6.89 (1H, s).

Example 71

5-[1-Hydroxy-1-(4-methyloxazol-2-yl)]methylene-2-thioxothiazolidin-4-one (Compound I-71)

m.p.: 203–205° C. recrystallization solvent: isopropanol Anal. Calcd for $C_8H_6N_2O_3S_2$: C, 39.66; H, 2.50; N, 11.56; S, 26.47. Found: C, 39.64; H, 2.57; N, 11.32; S, 25.95. NMR($d_6$-DMSO) δ: 2.22(3H, d, J=1.5 Hz), 8.17(1H, d, J=1.5 Hz).

Example 72

5-[1-Hydroxy-1-(5-propyloxazol-2-yl)]methylene-2-thioxothiazolidin-4-one (Compound I-72)

m.p.: 188–192° C. (decomposition) recrystallization solvent: isopropanol Anal. Calcd for $C_{10}H_{10}N_2O_3S_2$: C, 44.43; H, 3.73; N, 10.36; S, 23.72. Found: C, 44.26; H, 3.59; N, 10.30; S, 24.10. NMR($d_6$-DMSO) δ: 0.94(3H, t, J=7.2 Hz), 1.66(2H, m), 2.75(2H, t, J=7.2 Hz), 7.38(1H, s).

Example 73

5-[1-Hydroxy-1-(4-methylfuran-2-yl)]methylene-2-thioxothiazolidin-4-one (Compound I-73)

m.p.: 242–245° C. (decomposition) recrystallization solvent: isopropanol Anal. Calcd for $C_9H_7NO_3S_2$: C, 44.80; H, 2.92; N, 5.80; S, 26.58. Found: C, 44.53; H, 2.80; N, 5.83; S, 26.50. NMR($d_6$-DMSO) δ: 2.06(3H, s), 7.38(1H, s), 7.93(1H, s), 13.6(2H, brs).

Example 74

5-[1-(4-Chlorothiophen-2-yl)-1-hydroxy]methylene-2-thioxothiazolidin-4-one (Compound I-74)

m.p.: 228–232° C. (decomposition) recrystallization solvent: isopropanol Anal. Calcd for $C_8H_4ClNO_2S_3$: C, 34.59; H, 1.45; Cl, 12.76; N, 5.04; S, 34.63. Found: C, 34.60; H, 1.37; Cl, 12.70; N, 5.09; S, 34.35. NMR($d_6$-DMSO) δ: 7.75(1H, s), 8.63(1H, s), 12.4(1H, brs).

Example 75

5-[1-[4-(3-Cyanopropyloxy)]phenyl-1-hydroxy]methylene-2-thioxothiazolidin-4-one (Compound I-75)

m.p.: 172–177° C. recrystallization solvent: isopropanol Anal. Calcd for $C_{14}H_{12}N_2O_3S_2$ $0.38H_2O$: C, 51.40; H, 3.93; N, 8.56; S, 19.60. Found: C, 51.47; H, 3.75; N, 8.49; S, 20.05. NMR($d_6$-DMSO) δ: 2.06(2H, m), 2.67(2H, m), 4.13 (2H, m), 7.10(2H, d, J=8.8 Hz), 7.70(2H, d, J=8.8 Hz).

Example 76

5-[1-Hydroxy-1-(5-methyl-4,5-dihydrooxazol-2-yl)]methylene-2-thioxothiazolidin-4-one (Compound I-76)

m.p.: 184–185° C. recrystallization solvent: diisopropyl ether Anal. Calcd for $C_8H_8N_2O_3S_2$ $1.25H_2O$: C, 36.01; H, 3.97; N, 10.50; S, 24.04. Found: C, 36.28; H, 3.73; N, 10.38; S, 23.84. NMR($d_6$-DMSO) δ: 1.02(3H, d, J=6.6 Hz), 3.14 (2H, t, J=6.0 Hz), 3.75 (1H, m), 8.74(1H, brs), 9.36(1H, brs).

Example 77

5-[1-[2-(3-Cyanopropyloxy)]phenyl-1-hydroxy-]methylene-2-thioxothiazolidin-4-one sodium salt (Compound I-77)

Foamy Powder Anal. Calcd for $C_{14}H_{11}N_2O_3S_2Na_{1.2}H_2O$ $0.125C_4H_8O_2$: C, 46.27; H, 3.72; N, 7.49; Na, 7.38; S, 17.16. Found: C, 46.31; H, 3.50; N, 7.29; Na, 7.40; S, 16.90. NMR($d_6$-DMSO) δ: 2.11(2H, m), 2.74(2H, t, J=7.2 Hz), 4.20(2H, t, J=7.2 Hz), 7.00–7.80(4H, m).

Example 78

5-[1-Hydroxy-1-(5-methyl-1H-1,2,4-triazol-3-yl)]methylene-2-thioxothiazolidin-4-one (Compound I-78)

m.p.: >300° C. (decomposition) recrystallization solvent: methanol Anal. Calcd for $C_7H_6N_4O_2S_2$: C, 34.70; H, 2.50; N, 23.12; S, 26.47. Found: C, 34.54; H, 2.42; N, 22.86; S, 26.78. NMR($d_6$-DMSO) δ: 3.16(3H, s), 13.8(3H, brs).

Example 79

5-[1-Hydroxy-1-[(4-hydroxymethyl-5-methyl)oxazol-2-yl)]methylene-2-thioxothiazolidin-4-one (Compound I-79)

m.p.: 145–151° C. (decomposition) recrystallization solvent: isopropanol Anal. Calcd for $C_9H_8N_2O_4S_2$ $0.1C_3H_8O$: C, 40.35; H, 3.30; N, 9.96; S, 22.80. Found: C, 40.28; H, 2.94; N, 9.63; S, 22.19. NMR($d_6$-DMSO) δ: 2.43(3H, s), 4.55(2H, s).

Example 80

5-[1-[(5-Ethoxy-4-ethoxycarbonyl)oxazol-2-yl)-1-hydroxy]methylene-2-thioxothiazolidin-4-one (Compound I-80)

m.p.: 200–205° C. (decomposition) recrystallization solvent: isopropanol Anal. Calcd for $C_{12}H_{12}N_2O_6S_2$: C, 41.85; H, 3.51; N, 8.13; S, 18.62. Found: C, 41.68; H, 3.48; N, 8.02; S, 18.41. NMR($d_6$-DMSO) δ: 1.27(3H, t, J=7.2 Hz), 1.41 (3H, t, J=7.2 Hz), 4.26 (2H, q, J=7.2 Hz), 4.58(2H, q, J=7.2 Hz).

Example 81

5-[1-(4-Carboxy-5-ethoxyoxazol-2-yl)-1-hydroxy]methylene-2-thioxothiazolidin-4-one (Compound I-81)

m.p.: >300° C. (decomposition) recrystallization solvent: isopropanol/n-hexane NMR($d_6$-DMSO) δ: 1.38(3H, t, J=7.0 Hz), 4.49(2H, q, J=7.0 Hz), 12.7 (1H, brs).

Example 82

5-[(]-Furan-2-yl)-1-hydroxy]methylene-imidazolidine-2,4-dione (Compound I-82)

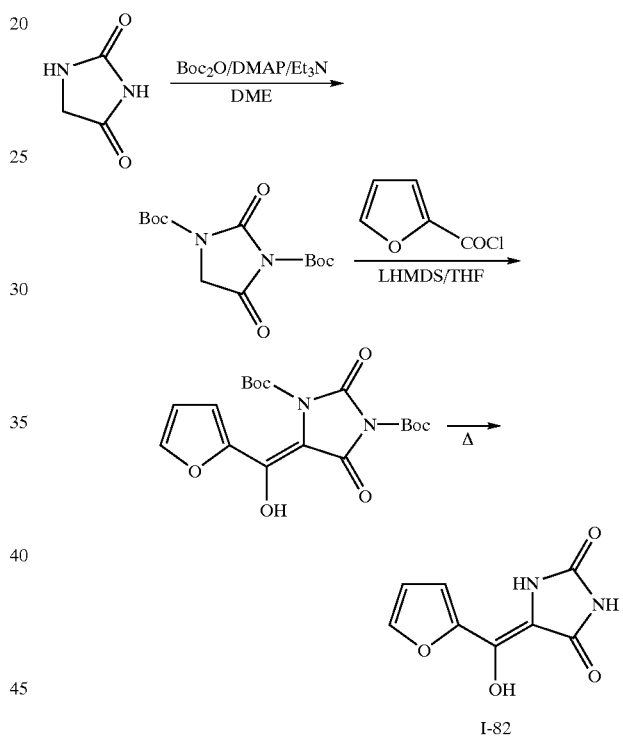

(1) To a solution of hydantoin (3.0 g, 30 mmol) in DME (120 ml) were added di-tert-butylcarbonate (27 g, 126 mmol), DMAP (67 mg, 0.55 mmol), and trietylamine (3.1 g, 30.6 mmol) sequentially at room temperature. The reaction mixture was allowed to stand at room temperature overnight and concentrated under reduced pressure. Water was added to the residue and the solution was extracted with ethyl acetate. The extract was washed with water, dried, and concentrated under reduced pressure. The residue was subjected to silica gel column chromatography. Fractionation eluted by chloroform/ethyl acetate (v/v, 9/1) was concentrated to give 1,3-di-tert-butoxycarbonylimidazolidine-2,4-dione (810 mg, 9%) as a oil.

NMR(CDCl₃) δ: 1.56(9H, s), 1.58(9H, s), 4.23(2H, s).
(2) To a solution of above obtained compound (300 mg, 1 mmol) in THF (10 ml) was added dropwise THF solution of lithium bis(trimethylsilyl)amide (1M, 1.5 mL, 1.5 mmol) at −78—−68° C. After the reaction mixture was stirred at the same temperature for 30 min, a solution of 2-furoyl chloride (0.26 g, 2 mmol) in THF (3 ml) was added thereto. The reaction mixture was stirred at the same temperature for 30 min and at room temperature for 2.5 h. The reaction mixture was poured into ice-water containing a aqueous solution of 1 mol/L citric acid (2 mL), extracted two times with ethyl acetate, washed with a saturated aqueous solution of sodium hydrogen carbonate and brine, and dried. The solvent was evaporated and the residual oil was powdered by n-hexane to give 5-[(1-furan-2-yl)-1-hydroxy]methylene-1,3-(di-tert-butoxycarbonyl)imidazolidine-2,4-dione (280 mg, 71%).

NMR(CDCl$_3$) δ: 1.44(9H, s), 1.56(9H, s), 5.78(1H, s), 6.68(1H, dd, J=1.5, 3.9 Hz), 7.48(1H, d, J=3.9 Hz), 7.60(1H, J=1.5 Hz).

(3) The above compound (100 mg, 0.25 mmol) was heated at 120° C. without solvent. After cooling, the residue was washed with ethanol and filtered to give the title compound (25 mg, 51%).

m.p.: 220–222° C. (decomposition) recrystallization solvent: ethanol Anal. Calcd for $C_8H_6N_2O_4$ 0.1H$_2$O: C, 49.04; H, 3.19; N, 14.30. Found: C, 48.94; H, 3.18; N, 14.61. NMR(d$_6$-DMSO) keto-type δ: 5.69(1H, s), 6.84(1H, d, J=3.6 Hz), 7.74(1H, d, J=3.6 Hz),8.16(1H, s), 8.24(1H, s), 11.0(1H, brs).

Experiment Example

The later-mentioned experimental examples were done by using the above-mentioned compound.

Experiment Example 1

Inhibitory Activity Against HCV RNA-Dependent RNA Polymerase (1) Preparation of Hepatitis C Virus (HCV) RNA-Dependent RNA Polymerase It was collected several cDNA clones of HCV RNA-dependent RNA polymerase from plasma of people infected with HCV, RNA-dependent RNA polymerase was expressed by using insect cell or *E. coli* from these clones. RNA-dependent RNA polymerase in cell extract was purified by anion-exchange chromatography, heparin-affinity chromatography, poly U-affinity chromatography, cation-exchange chromatography, gel filtration chromatography, and the like. The preparation was done at about 4° C. under low temperature condition, as solution dissolving enzyme was used Tris buffer (pH 7.5) containing ethylenediamine tetraacetic acid (1 mM), dithiothreitol (10 mM), and glycerol (20%). The purified enzyme was kept at 4° C. or −20° C. until it was used for assay.

(2) Method of HCV RNA-Dependent RNA Polymerase Assay

①  In polypropylene vessel was added buffer I*[1)](10.5 μL) containing Tris-HCl (100 mM, pH 7.5), magnesium chloride (25 mM), dithiothreitol (5 mM), potassium chloride (125 mM), ethylenediamine tetraacetic acid (5 mM), and then were added poly(A)*[2)] aqueous solution (100 μg/mL, 10.5 μL), oligo(U)$_{12}$*[3)] aqueous solution (10 μg/mL, 10.5 μL), and water (8 μL), and the mixture was mixed slowly.

*1) All of water used as experimental material in enzyme reaction were carried out inactivation treatment of Rnase with diethylpyrocarbonate. The inactivation treatment with diethylpyrocarbonate was carried out as follows, 1) diethylpyrocarbonate (0.1 g) was dissolved in de-ionized water (100 mL), 2) the solution was stood at 37° C. for 24 h, 3) kept in autoclave at 120° C. for 30 min.
*2) Poly(A) is single strand polynucleotide composed with only adenylic acid. It was used as template.
*3) Oligo(U)$_{12}$ is single strand oligonucleotide composed with only 12 element of uridylic acid. It was used as primer.

② Next, to the mixture was added a solution (10.5 μL) of RNA-dependent RNA polymerase, and preincubation was carried out at 25° C. for 60 min.

③ A solution (50 μL) preincubated described in ② was added into 96-wells microtiter plate divided test compound (5.26 μL per well) dissolved with dimethylsulfoxide or water.

④ Moreover, to the mixture was added a mixed solution (50 μL) of water (39.4 μL) and buffer II (10.6 μL) containing Tris-HCl (100 mM, pH 7.5), magnesium chloride (25 mM), dithiothreitol (5 mM), potassium chloride (125 mM), ethylenediamine tetraacetic acid (5 mM), and UTP[4)] (2.1 μM, containing 1 μCi$^3$H-UTP) and the mixture was mixed, and the enzyme reaction was carried out at 25° C. for 30 min.

*4) UTP is uridine triphosphate. It was used as substrate.

⑤ When the enzyme reaction was passed for 30 min, to the mixture was added a aqueous solution (50 mM, 50 μL) of ethylenediamine tetraacetic acid disodium and the enzyme reaction was stopped.

⑥ Next, after all volume of sample of ⑤ was transferred on filter introduced diethylaminoethyl group (henceforth shortening as DEAE-filter mat) by using cell harvester, was carried the washing twice with sodium phosphate buffer (0.25 M, pH 7.0) for 10 sec and the washing once with deionized water for 10 sec.

⑦ After the washing, DEAE-filter mat was dried at 95° C. for 15 min and sealed together with liquid scintillator (10 mL) into sample bag.

⑧ Radioactivity was measured by using scintillation counter.

⑨ The percentage of inhibition was calculated by replacing the measured value of radioactivity (unit; ccpm) into the following expression.

The percentage of inhibition=100−(the measured value in presence of test compound−the measured value in absence of enzyme)÷(the measured value in absence of test compound−the measured value in absence of enzyme)×100.

+e,crc +b 10+ee The concentration of test compound inhibiting 50% (IC$_{50}$) was obtained from the percentage of inhibition calculated in ⑨ and the used concentration of test compound inhibiting.

In case of the percentage of inhibition is A % when α μg/mL of the compound is used and the percentage of inhibition is B % when β μg/ml of the compound is used, IC$_{50}$ was obtained from the following expression. Provided that it is theorized as A≧50>B.

$$IC_{50}(\text{unit}; \mu g/mL)=10^{\{(50-B)/(A-B)\times\log \alpha-\log \beta\}+\log \beta\}}$$

Experiment Example 2

Inhibitory Activity Against BVDV RNA-Dependent RNA Polymerase

Inhibitory activity against RNA-dependent RNA polymerase (RdRp) of bovine virus diarrhea virus (BVDV) was experimented too in the same way in experiment example 1.

The results of experiment example 1 and experiment example 2 are shown in Table 1.

TABLE 1

| Compound Number | Experimental example 1 IC$_{50}$ for HCV RdRp (μg/mL) | Experimental example 2 IC$_{50}$ for BVDV RdRp (μg/mL) |
|---|---|---|
| I-1 | 0.25 | 2.5 |
| I-2 | 0.90 | 18 |
| I-22 | 4.9 | 37 |

TABLE 1-continued

| Compound Number | Experimental example 1<br>IC$_{50}$ for HCV RdRp ($\mu$g/mL) | Experimental example 2<br>IC$_{50}$ for BVDV RdRp ($\mu$g/mL) |
|---|---|---|
| I-27 | 1.6 | 18 |
| I-28 | 7.1 | 24 |
| I-29 | 1.8 | 27 |
| I-30 | 6.8 | 32 |
| I-32 | 3.2 | 37 |
| I-34 | 0.92 | 14 |
| I-35 | 1.4 | 34 |
| I-36 | 7.6 | 38 |
| I-37 | 3.0 | 36 |
| I-40 | 2.0 | 5.3 |

Formulation Example

The following formulation examples are provided to further illustrate the present invention and are not to be construed as limiting the scope thereof. The tern "active ingredient" used herein means a compound used in the present invention, a tautomer, a prodrug, a pharmaceutical acceptable salt, or a salt thereof.

Formulation Example 1

Hard gelatin capsules are prepared using of the following ingredients:

| | Dose (mg/capsule) |
|---|---|
| Active ingredient | 250 |
| Starch, dried | 200 |
| Magnesium stearate | 10 |
| Total | 460 mg |

Formulation Example 2

A tablet is prepared using of the following ingredients:

| | Dose (mg/tablet) |
|---|---|
| Active ingredient | 250 |
| Cellulose, microcrystals | 400 |
| Silicon dioxide, fumed | 10 |
| Stearic acid | 5 |
| Total | 665 mg |

The components are blended and compressed to form tablets each weighing 665 mg.

Formulation Example 3

An aerosol solution is prepared containing the following components:

| | Weight |
|---|---|
| Active ingredient | 0.25 |
| Ethanol | 25.75 |
| Propellant 22 (chlorodifluoromethane) | 74.00 |
| Total | 100.00 |

The active compound is mixed with ethanol and the admixture is added to a portion of the propellant 22, cooled to −30° C. and transferred to a filling device. The required amount is then fed to a stainless steel container and diluted with the reminder of the propellant. The valve units are then fitted to the container.

Formulation Example 4

Tablets, each containing 60 mg of active ingredient, are made as follows.

| | |
|---|---|
| Active ingredient | 60 mg |
| Starch | 45 mg |
| Microcrystals cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch, and cellulose are passed through a No. 45 mesh U.S. sieve, and the mixed thoroughly. The aqueous solution containing polyvinylpyrrolidone is mixed with the resultant powder, and the admixture then is passed through a No. 14 mesh U.S. sieve. The granules so produced are dried at 50° C. and passed through a No. 18 mesh U.S. sieve. The sodium carboxymethyl starch, magnesium stearate, and talc, previously passed through No. 60 mesh U.S. sieve, are then added to the granules which, after mixing, are compressed on a tablet machine to yield tablets each weighing 150 mg.

Formulation Example 5

Capsules, each containing 80 mg of active ingredient, are made as follows:

| | |
|---|---|
| Active ingredient | 80 mg |
| Starch | 59 mg |
| Microcrystals cellulose | 59 mg |
| Magnesium stearate | 2 mg |
| Total | 200 mg |

The active ingredient, cellulose, starch, and magnesium stearate are blended, passed through a No. 45 mesh U.S. sieve, and filled into hard gelatin capsules in 200 mg quantities.

Formulation Example 6

Suppository, each containing 225 mg of active ingredient, are made as follows:

| Active ingredient | 225 mg |
| --- | --- |
| Saturated fatty acid glycerides | 2000 mg |
| Total | 2225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation Example 7

Suspensions, each containing 50 mg of active ingredient per 5 mL dose, are made as follows:

| Active ingredient | 50 mg |
| --- | --- |
| Sodium carboxymethyl cellulose | 50 mg |
| Syrup | 1.25 mL |
| Benzoic acid solution | 0.10 mL |
| Flavor | q.v. |
| Color | q.v. |
| Purified water to total | 5 mL |

The active ingredient is passed through a No. 45 U.S. sieve, and mixed with the sodium carboxymethyl cellulose and syrup to form a smooth paste. The benzoic acid solution, flavor and color are diluted with a portion of the water and added, with stirring. Sufficient water is then added to produce the required volume.

Formulation Example 8

An intravenous formulation may be prepared as follows:

| Active ingredient | 100 mg |
| --- | --- |
| Isotonic saline | 1000 mL |

The solution of the above ingredients is generally administered intravenously to a subject at a rate of 1 mL per minute.

Industrial Applicability

The compound of the formula (I) or (II) exhibits an inhibitory activity against a nucleic acid polymerase, in detail an inhibitory activity against a RNA-dependent RNA polymerase. Therefore, hepatitis C virus and the like can be treated with an inhibitory agent against a RNA-dependent RNA polymerase which contains the compound of the formula (I) or (II).

What is claimed is:

1. A method of treating hepatitis C comprising administration of a treating agent against hepatitis C which contains as an active ingredient a compound of the formula (I), a tautomer, a prodrug, a pharmaceutically acceptable salt, or a solvate thereof:

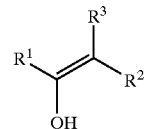

(I)

wherein $R^1$ is an optionally substituted carbocyclic group or an optionally substituted heterocyclic group; $R^2$ and $R^3$ taken together with the adjacent carbon atom form an optionally substituted heterocyclic group having one or more of oxo and/or thioxo.

2. The method as described in claim 1 wherein $R^1$ is optionally substituted heteroaryl or optionally substituted aryl; $R^2$ and $R^3$ taken together with the adjacent carbon atom form a group of the formula (A):

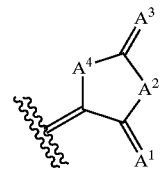

(A)

wherein $A^1$ and $A^3$ are each independently oxygen atom or sulfur atom; $A^2$ and $A^4$ are each independently —O—, —S—, or —NR$^4$— wherein $R^4$ is hydrogen, alkyl, acyl, optionally substituted aryl, or optionally substituted aralkyl.

3. A treating agent against hepatitis C which contains as an active ingredient a compound of the formula (I), a tautomer, a prodrug, a pharmaceutically acceptable salt, or a solvate thereof:

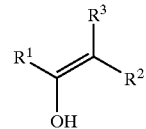

(I)

wherein $R^1$ is optionally substituted heteroaryl or optionally substituted aryl; $R^2$ and $R^3$ taken together with the adjacent carbon atom form a group of the formula (A):

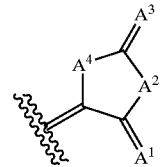

(A)

wherein $A^1$ is oxygen atom; $A^2$ is —NH—; $A^3$ and $A^4$ are —S—.

4. A compound of the formula (II):

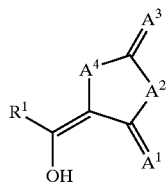

wherein $R^1$ is optionally substituted carbocyclic group or optionally substituted heterocyclic group; $A^1$ and $A^3$ are each independently oxygen atom or sulfur atom; $A^2$ is —$NR^4$— wherein $R^4$ is hydrogen, optionally substituted alkyl, optionally substituted acyl, optionally substituted aryl, or optionally substituted aralkyl, provided that when $R^1$ is optionally substituted aryl, $R^4$ is hydrogen or optionally substituted alkyl; $A^4$ is —S—; and provided that the following compounds are excluded wherein $A^1$ is oxygen atom, $A^2$ is —NEt-, $A^3$ is sulfur atom, and $R^1$ is 4-bromophenyl, 4-n-butoxycarbonylphenyl, 4-methoxyphenyl, 3-nitrophenyl, 4-nitrophenyl, 3-methylphenyl, 4-methylphenyl, 4-chlorophenyl or phenyl; $A^1$ is oxygen atom, $A^2$ is —NH—, $A^3$ is sulfur atom, and $R^1$ is 2-thiocarboxyphenyl or 2-carboxyphenyl; and $A^1$ is oxygen atom, $A^2$ is —NH—, $A^3$ is oxygen atom, and $R^1$ is 2-carboxyphenyl;

a tautomer, a prodrug, a pharmaceutically acceptable salt, or a solvate thereof.

5. A compound of claim 4 wherein $R^1$ is optionally substituted heteroaryl; a tautomer, a prodrug, a pharmaceutically acceptable salt, or a solvate thereof.

6. A compound of claim 4 wherein $R^1$ is non-substituted heteroaryl or heteroaryl substituted with alkyl, alkoxy, hydroxy, halogen, trityl, alkoxyalkoxy, cyanoallylalkoxy, cyanoalkoxy, hydroxyalkyl, cyanoalkyl, carboxy or alkoxycarbonyl;

a tautomer, a prodrug, a pharmaceutically acceptable salt, or a solvate thereof.

7. A compound of claim 5 wherein $R^1$ is optionally substituted 5-membered heteroaryl;

a tautomer, a prodrug, a pharmaceutically acceptable salt, or a solvate thereof.

8. A compound of claim 5 wherein $R^1$ is optionally substituted furyl, optionally substituted thienyl, optionally substituted pyrrolyl, optionally substituted imidazolyl, optionally substituted oxazolyl optionally substituted isoxazolyl, optionally substituted triazolyl, optionally substituted oxadiazolyl, optionally substituted tetrazolyl, optionally substituted pyridyl, optionally substituted benzofuryl, optionally substituted pyrimidinyl, optionally substituted pyrazinyl, or optionally substituted thiazolyl;

a tautomer, a prodrug, a pharmaceutically acceptable salt, or a solvate thereof.

9. A compound of claim 4 wherein $R^1$ is optionally substituted aryl;

a tautomer, a prodrug, a pharmaceutically acceptable salt, or a solvate thereof.

10. A compound of claim 4 wherein $A^2$ is —NH—;

a tautomer, a prodrug, a pharmaceutically acceptable salt, or a solvate thereof.

11. A compound of claim 4 wherein $A^1$ is oxygen atom; $A^3$ is sulfur atom;

a tautomer, a prodrug, a pharmaceutically acceptable salt, or a solvate thereof.

12. A compound of claim 4 wherein $A^1$ is oxygen atom; $A^2$ is —NH—;

$A^3$ is sulfur atom; $A^4$ is —S—;

a tautomer, a prodrug, a pharmaceutically acceptable salt, or a solvate thereof.

13. A pharmaceutical composition which contains as an active ingredient a compound of claim 4, a tautomer, a prodrug, a pharmaceutically acceptable salt, or a solvate thereof.

14. A pharmaceutical composition of claim 13 as a treating agent against hepatitis C.

15. A pharmaceutical composition of claim 13 as an anti-hepatitis C virus agent.

16. A pharmaceutical composition of claim 13 as a nucleic acid polymerase inhibitor.

17. A pharmaceutical composition of claim 13 as a RNA-dependent RNA polymerase inhibitor.

18. A method of treating hepatitis C comprising administration of a treating agent against hepatitis C of claim 3.

* * * * *